(12) United States Patent
Guenther et al.

(10) Patent No.: US 10,183,994 B2
(45) Date of Patent: Jan. 22, 2019

(54) ANTI-TNFα ANTIBODIES WITH PH-DEPENDENT ANTIGEN BINDING FOR IMPROVED TARGET CLEARENCE

(71) Applicant: Merck Patent GmbH, Darmstadt (DE)

(72) Inventors: Ralf Guenther, Griesheim (DE); Stefan Becker, Darmstadt (DE); Laura Rhiel, Frankfurt am Main (DE); Bjoern Hock, Maintal (DE); Christian Schroeter, Darmstadt (DE)

(73) Assignee: Merck Patent GmbH, Darmstadt (DE)

(*) Notice: Subject to any disclaimer, the term of this patent is extended or adjusted under 35 U.S.C. 154(b) by 0 days.

(21) Appl. No.: 15/322,893

(22) PCT Filed: Jun. 26, 2015

(86) PCT No.: PCT/EP2015/001296
§ 371 (c)(1),
(2) Date: Dec. 29, 2016

(87) PCT Pub. No.: WO2016/000813
PCT Pub. Date: Jan. 7, 2016

(65) Prior Publication Data
US 2017/0226199 A1    Aug. 10, 2017

(30) Foreign Application Priority Data

Jun. 30, 2014 (EP) .................... 14002231

(51) Int. Cl.
*A61K 39/395* (2006.01)
*C07K 16/00* (2006.01)
*C07K 16/24* (2006.01)
*A61K 47/48* (2006.01)
*A61K 39/00* (2006.01)

(52) U.S. Cl.
CPC ...... *C07K 16/241* (2013.01); *A61K 47/48546* (2013.01); *A61K 2039/505* (2013.01); *C07K 2317/21* (2013.01); *C07K 2317/52* (2013.01); *C07K 2317/56* (2013.01); *C07K 2317/565* (2013.01); *C07K 2317/76* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | | | |
|---|---|---|---|---|
| 7,217,797 B2 * | 5/2007 | Hinton | .................... | C07K 16/00 435/326 |
| 2011/0076275 A1 * | 3/2011 | Igawa | .............. | A61K 39/39591 424/136.1 |
| 2011/0111406 A1 | 5/2011 | Igawa et al. | | |
| 2011/0229489 A1 | 9/2011 | Pons et al. | | |
| 2012/0263731 A1 | 10/2012 | Fraunhofer et al. | | |
| 2013/0011866 A1 | 1/2013 | Igawa et al. | | |
| 2013/0247234 A1 | 9/2013 | Mcwhirter et al. | | |
| 2013/0303396 A1 | 11/2013 | Igawa et al. | | |
| 2013/0336963 A1 | 12/2013 | Igawa et al. | | |
| 2014/0271617 A1 | 9/2014 | Igawa et al. | | |
| 2014/0329711 A1 | 11/2014 | Murphy et al. | | |
| 2014/0377275 A1 | 12/2014 | Neu et al. | | |
| 2015/0139988 A1 * | 5/2015 | Labkovsky | .......... | C07K 16/241 424/133.1 |

FOREIGN PATENT DOCUMENTS

| | | |
|---|---|---|
| EP | 2 275 443 A1 | 1/2011 |
| EP | 2 762 564 A1 | 8/2014 |
| WO | 2011/111007 A2 | 9/2011 |
| WO | 2012/065072 A2 | 5/2012 |
| WO | 2013/046722 A1 | 4/2013 |

OTHER PUBLICATIONS

Paul, Fundamental Immunology, 3rd Edition, 1993, pp. 292-295, under the heading "Fv Structure and Diversity in Three Dimensions".*
Rudikoff et al Proc. Natl. Acad. Sci.USA, 79(6):1979-1983, Mar. 1982.*
Colman P. M. Research in Immunology, 145:33-36, 1994.*
Barrios et al J Molecular Recognition 17: 332-338, 2004.*
Pascalis et al The Journal of Immunology 169: 3076-3084, 2002.*
W. Ito, et al., "The His-probe method: effects of histidine residues introduced into the complementarity-determining regions of antibodies on antigen-antibody interactions at different pH values," FEBS Letters, vol. 309, No. 1, Aug. 1992, pp. 85-88, XP 8123385 A.
International Search Report dated Sep. 7, 2015 in PCT/EP2015/001296 filed Jun. 26, 2015.
Bharat B. Aggarwal, "Signalling Pathways of the TNF Superfamily: A Double-Edged Sword" Nature Reviews Immunology, vol. 3, Sep. 2003, pp. 745-756.
Saurabh Rob Aggarwal, "What's Fueling the Biotech Engine—2012 to 2013" Nature Biotechnology, vol. 32, No. 1, Jan. 2014, pp. 32-39.
Cédric Atmanene, et al., "Extending Mass Spectrometry Contribution to Therapeutic Monoclonal Antibody Lead Optimization: Characterization of Immune Complexes Using Noncovalent ESI-MS" Analytical Chemistry, vol. 81, No. 15, Aug. 1, 2009, pp. 6364-6373.
Eric T. Boder, et al., "Yeast Surface Display for Screening Combinatorial Polypeptide Libraries" Nature Biotechnology, vol. 15, Jun. 1997, pp. 553-557.

(Continued)

*Primary Examiner* — Shulamith H Shafer
(74) *Attorney, Agent, or Firm* — Grüneberg and Myers PLLC

(57) ABSTRACT

The invention relates to anti-TNFα antibodies which are engineered to exhibit a pH-sensitive antigen binding. The invention is preferably directed to anti-TNFα antibody adalimumab (Humira®) or biologically active variants and fragments thereof, wherein the original adalimumab antibody or variant or fragment thereof is engineered by modifications of amino acid sequence within the variable regions. Specifically, the invention relates to adalimumab or biologically active variants or fragments thereof, wherein the CDR domains are modified by replacing one or more amino acid residues by histidine residues.

Figure 1:
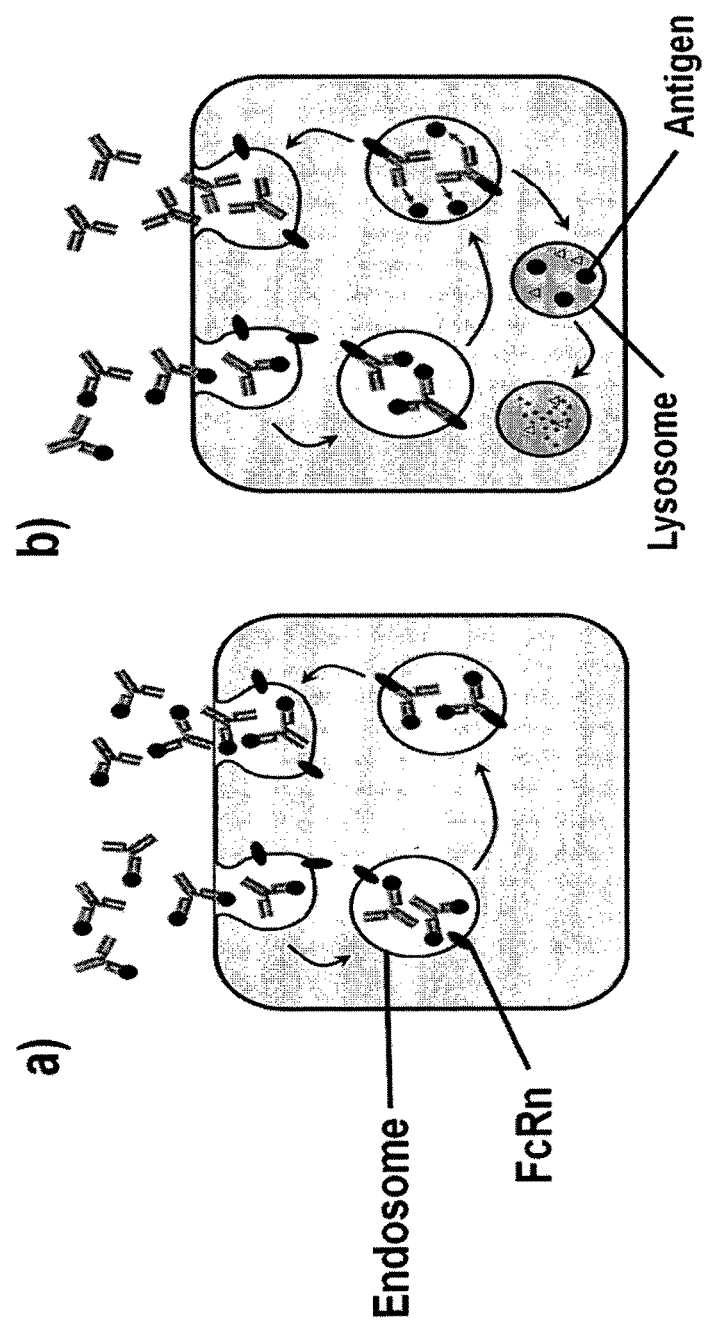

22 Claims, 14 Drawing Sheets
Specification includes a Sequence Listing.

(56) References Cited

OTHER PUBLICATIONS

Paul J. Carter, "Introduction to Current and Future Protein Therapeutics: A Protein Engineering Perspective" Experimental Cell Research, vol. 317, 2011, pp. 1261-1269.
Javier Chaparro-Riggers, et al., "Increasing Serum Half-Life and Extending Cholesterol Lowering in Vivo by Engineering Antibody with pH-Sensitive Binding to PCSK9" The Journal of Biological Chemistry, vol. 287, No. 14, Mar. 30, 2012, pp. 11090-11097 and cover page.
Ernest H.S. Choy, et al., "Cytokine Pathways and Joint Inflammation in Rheumatoid Arthritis" The New England Journal of Medicine, vol. 344, No. 12, Mar. 22, 2001, pp. 907-916.
William F. Dall'Acqua, et al., "Properties of Human IgG1s Engineered for Enhanced Binding to the Neonatal Fc Receptor (FcRn)" The Journal of Biological Chemistry, vol. 281, No. 33, Aug. 18, 2006, pp. 23514-23524 and cover page.
Marc Feldmann, Development of Anti-TNF Therapy for Rheumatoid Arthritis Nature Reviews Immunology, vol. 2, May 2002, pp. 364-371.
Fred D. Finkelman, et al., "Anti-Cytokine Antibodies as Carrier Proteins. Prolongation of in Vivo Effects of Exogenous Cytokines by Injection of Cytokine-Anti-Cytokine Antibody Complexes" The Journal of Immunology, vol. 151, No. 3, Aug. 1, 1993, pp. 1235-1244 and cover page.
Nimish Gera, et al., "Design of pH Sensitive Binding Proteins from the Hyperthermophilic Sso7d Scaffold" PLOS ONE, vol. 7, Nov. 2012, pp. 1-14.
Takahiko Horiuchi, et al., "Transmembrane TNF-α: Structure, Function and Interaction with Anti-TNF Agents" Rheumatology. vol. 49, 2010, pp. 1215-1228.
Tomoyuki Igawa, et al., "Antibody Recycling by Engineered pH-Dependent Antigen Binding Improves the Duration of Antigen Neutralization" Nature Biotechnology, vol. 28, No. 11, Nov. 2010, pp. 1203-1207 and extra page.
Tomoyuki Igawa, et al., "Engineered Monoclonal Antibody with Novel Antigen-Sweeping Activity In Vivo" PLOS ONE, vol. 8, May 2013, pp. 1-10.
Zehra Kaymakcalan, et al., "Comparisons of Affinities, Avidities, and Complement Activation of Adalimumab, Infliximab, and Etanercept in Binding to Soluble and Membrane Tumor Necrosis Factor" Clinical Immunology, vol. 131, 2009, pp. 308-316.
Timothy T. Kuo, et al., "Neonatal Fc Receptor and IgG-Based Therapeutics" mAbs, vol. 3, 2011, pp. 422-430 and cover page.
Megan L. Murtaugh, et al., "A Combinatorial Histidine Scanning Library Approach to Engineer Highly pH-Dependent Protein Switches" Protein Science, vol. 20, 2011, pp. 1619-1631.
Derry C. Roopenian, et al., "FcRn: The Neonatal Fc Receptor Comes of Age" Nature Reviews Immunology, vol. 7, Sep. 2007, pp. 715-725.
Casim A. Sarkar, et al., "Rational Cytokine Design for Increased Lifetime and Enhanced Potency Using pH-Activated "Histidine Switching"" Nature Biotechnology, vol. 20, Sep. 2002, pp. 908-913.
Vernon F. Schabert, et al., "Costs of Tumor Necrosis Factor Blockers Per Treated Patient Using Real-World Drug Data in a Managed Care Population" Journal of Managed Care Pharmacy, vol. 19, No. 8, Oct. 2013, pp. 621-630.
Arndt J. G. Schuttelius, et al., "Biology of Tumor Necrosis Factor-α—Implications for Psoriasis" Experimental Dermatology, vol. 13, 2004, pp. 193-222.
Daniel Tracey, et al., "Tumor Necrosis Factor Antagonist Mechanisms of Action: A Comprehensive Review" Pharmacology & Therapeutics, vol. 117, 2008, pp. 244-279.
H Wajant, et al., "Tumor Necrosis Factor Signaling" Cell Death and Differentiation, 2003, pp. 45-65.

* cited by examiner

ANTI-TNFα ANTIBODIES WITH PH-DEPENDENT ANTIGEN BINDING FOR IMPROVED TARGET CLEARENCE

This application is a National Stage entry under § 371 of international Application No. PCT/EP2015/001296, filed on Jun. 26, 2015, and which claims the benefit of European Application No. 14002231.0, filed on Jun. 30, 2014.

FIELD OF THE INVENTION

The invention relates to anti-TNFα antibodies which are engineered to exhibit a pH-sensitive antigen binding. The invention is preferably directed to anti-TNFα antibody adalimumab (Humira®) or biologically active variants and fragments thereof, wherein the original adalimumab antibody or variant or fragment thereof is engineered by modifications of amino acid sequence within the variable regions. Specifically, the invention relates to adalimumab or biologically active variants or fragments thereof, wherein the CDR domains are modified by replacing one or more amino acid residues by histidine residues.

The resulting modified anti-TNFα antibodies elicit improved pharmacokinetic properties with improved antigen-mediated IgG clearance and extended over-all serum half life.

BACKGROUND OF THE INVENTION

It is believed that therapeutic antibodies (mAbs) at least offer important treatment options for many diseases like inflammatory, autoimmune or oncological disorders. In 2012 there were 40 FDA-approved mAbs on the US market against various targets in oncology and anti-inflammatory disorders with ~38.5% share within the biologics market. Sales of ~$24.6 billion manifest the role of therapeutic antibodies as highest earning category of all biologics (Aggarwal, 2009, Aggarwal, 2014).

For therapeutic antibodies different biological outcomes are determined by the interaction profiles with four classes of naturally occurring interaction partners: antigen, neonatal Fc-receptor (FcRn), Fc-receptors (FcγRs), and factors of the complement system (Chan and Carter, 2010). Several strategies have been reported to optimize antibodies that aim for additional or improved functions and specificities. (Beck et al, 2010). Within antibodies there are two structural features that can be addressed for engineering. First, the variable fragment (Fv) that mediates interaction with the antigen, second the constant fragment (Fc) that is involved in antibody recycling or mediates interactions with immune cells.

For different antigens (e.g. cytokines and growth factors) there are multiple mechanisms of action, e.g. blocking of soluble ligands thereby preventing the interaction to its corresponding receptor or blocking of the receptor itself. (Chan and Carter, 2010). A lot of effort has been invested on improving functions towards Fv-engineering that is often valued by increasing specificity and/or binding affinity to respective antigens (Beck et al, 2010). One strategy to elevate antibody efficacy is to enhance the Fv—antigen interaction by affinity maturation approaches. Herein the use of display technologies for screening molecule libraries allows isolation of variants that exhibit superior affinity.

The constant fragment (Fc) and its linked properties can be modulated with altered outcomes for immunity or antibody recycling. Prominent examples for altered Fc-mediated immune functions are enhanced antibody-dependent cellular cytotoxicity (ADCC) and complement-dependent cytotoxicity (CDC) that have been addressed to enhance antibody efficacy and to reduce the dosages.

Further strategies have been explored including direct and indirect arming of antibodies or modulation of specificities within multivalent antibodies (Carter 2011).

One important aspect of Fc-function corresponds to its critical role in antibody recycling that determines the long serum half life of human immunoglobulin 1 (IgG1). After cellular absorption via fluid phase pinocytosis, the Fc-portion of an IgG1 interacts in a pH-dependent manner with the neonatal Fc-receptor (FcRn) that leads to antibody capture in the acidified endosome (Kuo and Aveson, 2011). From there, antibodies are recycled back to the circulation and therefore can be protected from intracellular catabolism. Different mutational Fc-species with enhanced FcRn binding affinity were generated and tested for increased recycling rates with up to 4-fold extended serum half-life in cynomolgus studies by substituting three amino acids (Dall'Acqua et al, 2006).

Although most antibodies demonstrate highly efficient antigen blocking, there are drawbacks that are not fully addressed in the development process of therapeutic antibodies:

- In many therapeutic antibodies the antigen-binding sites bind to only one antigen molecule during the antibody's lifetime in plasma (Igawa et al, 2010).
- The dosing and frequency of antibody injections depends on the antigen synthesis rate between two injections as antigens are usually produced continuously in vivo (Igawa et al, 2010).
- High production costs & administration of large quantities of antibodies: Tocilicumab therapy: 8 mg/kg/month by i.v. (Maini et al, 2006), Adalimumab therapy: 40 mg every other week ($19,272/per person/per year (Schabert et al. 2013).
- When antibodies bind soluble targets "antibody buffering" effects can occur in which the degradation of the antigen is prevented while being bound to the antibody. A pool of free antigen establishes from reversible dissociation of the antigen-antibody complex and therefore prolongs the in vivo persistence (O'Hear and Foote, 2005)/Finkelman et al, 1993)

Considering these drawbacks of therapeutic antibodies, there is a need for more efficient molecules that produce therapeutic responses without high dosing and/or frequent administration (Chapparo-Riggers et al, 2012).

One possibility to achieve these goals is the specific engineering of the variable and optionally the constant region of a new or well established and approved antibody. One approach is to develop antibodies that exhibit pH-sensitive antigen binding. It has been shown that rational or combinatorial incorporation of histidines in the binding interfaces of antibodies and other proteins (Sarkar et al., 2002, Chaparro-Riggers et al., 2012, Ito et al., 1992, Igawa et al., 2010, Igawa et al., 2013, Murtaugh et al., 2011, Gera et al., 2012) can be commonly used to engineer pH-dependent binding. The basis for the pH-sensitive binding arises from the histidine's sensitivity to get protonated as a result of lowered pH-values in the microenvironment. More in detail, the histidines need to undergo a pKa-change upon binding in order to get protonated in a physiological pH-range (Murtaugh et al., 2011). Protonation of histidine side chains in binding-interfaces can alter electrostatic interactions or may induce conformational changes that lead to pH-dependent differences in binding affinity (Gera et al., 2012). Balanced electrostatic and non-electrostatic components of the binding equilibrium determine the sensitivity of binding (Murtaugh et al., 2011).

Incorporation of pH-sensitivity into the antigen binding site can increase the number of antigen-binding cycles. Herein, pH-dependent antibodies bind with similar high or reduced sufficient affinity to their antigens at plasma pH (pH 7.4) and show decreased binding at acidic pH (pH 6) (Chaparro-Riggers et al., 2012, Igawa et al, 2010) resulting in a faster and increased dissociation of the antibody from its antigen binding site within the acidic endosome, thereby enabling recycling back to the plasma and reducing antigen-mediated clearance.

During the FcRn-mediated recycling (FIG. 1*a*) of conventional antibodies that bind soluble targets, the antibody-antigen complex is recycled back to the extracellular space through the endosomal trafficking pathway (Roopenian and Akilesh, 2007). In contrast, pH-sensitive antibodies (FIG. 1*b*) release their antigen from the antibody-antigen complex during the endosomal acidification (pH<6.5) (Roopenian and Akilesh, 2007). As a result the free antibody gets recycled to the circulation whereas the antigen enters the degradative pathway (Chaparro-Riggers et al., 2012, Igawa et al, 2010).

The pH-sensitive binding therefore enables the antibody to interact with another antigen and allows the neutralization of multiple antigen molecules per antibody molecule. PH-sensitivity can also increase the half-life of antibodies that address membrane associated targets and internalize and degrade upon e.g. receptor binding. Herein pH-sensitivity can lead to increased half-life, when the antibody gets released during the endosomal acidification.

Several different strategies were published that aim for the engineering of pH-switches in proteins. Histidine (His) scanning by which every single amino acid residue (e.g. within the CDR regions) is mutated to His allows the characterization of single substitution variants and identification of effective mutations. Creation of new variants by combining these substitutions can result in enhanced pH-dependent binding (Murtaugh et al., 2011, Chaparro-Riggers et al., 2012, Igawa et al, 2010). Identification of residues that may contribute to pH-sensitivity upon replacement with histidines by structure-based modeling can help to minimize effort & time that is needed during the histidine scanning approach. Crystal structures are required in order to have a precise idea of residues that are critical for binding and the rational design of pH-switches (Sarkar et al., 2002). Combinatorial histidine scanning library approaches require in vitro screening technologies (e.g. phage display or yeast display) to isolate pH-sensitive variants from a large molecule library. Murtaugh and colleagues designed a llama VHH antibody library by using oligonucleotide-directed mutagenesis thereby allowing every residue within the binding interface to sample both histidine residues and wild-type residues of the parental VHH antibody. Towards screening of a M13-phage display library (diversity ~$10^{12}$) isolated variants showed KDs between 35-91 nM at pH 7.4 and a ~$10^4$ fold decrease in binding affinity at pH 5.4 (Murtaugh et al. 2011).

Since the recycled free antibody is capable of binding to another antigen, pH-dependent antigen binding would enable a single antibody molecule to repeatedly bind to multiple antigens, in contrast to the conventional approach in which a single antibody can bind to antigen only once.

Therefore, it is a general need to make available antibodies which are more effective with respect to their plasma and serum concentration, which can be achieved by installing pH sensitivity with respect to different cellular action sites of the therapeutic antibody.

SUMMARY OF THE INVENTION

The invention provides mutated forms of anti-TNFα antibody adalimumab (Humira®), wherein the mutation consists of one or more substitutions of amino acid residues of the original, non-mutated antibody adalimumab by histidine residues in the complementary determining regions (CDRs) of the heavy and/or light chain variable domains of the antibody. The introduction of histidine residues at defined position in some of the CDRs of adalimumab renders the original antibody much more pH-sensitive or pH-dependent compared to the non-mutated antibody. Interestingly, although the histidine-mutated antibody undergoes a significant loss of binding affinity (up to factor 10 and more of $K_D$) the mutated antibody of the invention is therapeutically significantly more effective compared to its parental non-mutated version, resulting in the possibility to reduce the antibody dosage or the antibody dosing intervals and thus the treatment costs significantly.

It has been shown by the invention that the successful introduction of histidine residues according to the invention by replacement of original amino acid residues in the CDRs of adalimumab or biologically active variants and fragments thereof, does not obey routine rules or mental considerations in view of the desired results regarding degree of pH-sensitivity and binding affinity.

Thus, it was found that histidine-mutated versions of adalimumab are specifically therapeutically effective, if the pH dependent antigen binding results in an antigen dissociation rate ($K_{dis}$) ratio pH 6/pH 7 which is 5-20 fold higher compared to the respective $K_{dis}$ rate ratio of non-mutated adalimumab, and the binding affinity of the mutated adalimumab is 1-25%, preferably 1-15%, more preferably 2-12% of the binding affinity of the non-histidine mutated adalimumab.

Therefore, the invention provides a human anti-TNFα antibody or an antigen binding fragment thereof with pH dependent antigen binding comprising the light and heavy chain variable regions of human antibody adalimumab or a variant thereof with same or similar biological activity, wherein at least one of the CDR domains of the light and/or the heavy chain variable regions is mutated by replacement of one or more amino acids within said CDR domains by a histidine residue, thus generating a mutated adalimumab or adalimumab variant eliciting a pH dependent antigen binding with an antigen dissociation rate ($K_{dis}$) ratio pH 6/pH 7 measured by Bioayer Interferometrie (Octet Red), or other comparable methods, which is at least 5, 10, 15 or 10 fold higher compared to the respective $K_{dis}$ rate ratio of non-mutated adalimumab.

In a further embodiment, the invention provides a respective mutated adalimumab, wherein the mutated antibody or antigen binding fragment thereof has a reduced antigen binding affinity, which is preferably 1-15%, respectively 1%, 2%, 3%, 4%, 5%, 6%, 7%, 8%, 9%, 10%, 11%, 12%, 13% 14% or 15% of the binding affinity of non-mutated adalimumab.

The invention provides human anti-TNFα antibodies deriving from adalimumab, wherein one or more original amino acid residues within the CDRs of parental adalimumab were replaced by histidine residues. Interestingly, the most effective histidine-mutated versions of adalimumab comprise histidine mutations within the variable light chain, especially in the CDR1 and CDR3 domains of the light chain. Preferred histidine-mutated adalimumab versions include further or independently a histidine-mutated CDR3 heavy chain.

Thus the invention provides mutated adalimumab or antigen binding fragment thereof comprising a CDR3 heavy chain sequence selected from the group consisting of:

```
                                      (SEQ ID NO: 12)
VSYHSTASSLDY (SEQ ID NO: 13)
VSYLSTAHHLDY (SEQ ID NO: 14)
VSYHSTAHHLDY (SEQ ID NO: 31)
VHYHSTASSLDY,
and (SEQ ID NO: 40)
VX₁YX₂STAX₃X₄LDY, wherein X₁ is S or H; X₂ is L or
H, X₃ = S or H, and X₄ is S or H, and wherein at
least X₁ or X₂ or X₃ or X₄ is H.
```

The invention further provides mutated adalimumab or antigen binding fragment thereof comprising a CDR3 light chain sequence selected from the group consisting of:

```
                                      (SEQ ID NO: 17)
HHYHRAPYT (SEQ ID NO: 18)
QHYHRAPYH (SEQ ID NO: 38)
QRHNRAPYT (SEQ ID NO: 19)
X₁HYHRAPYX₂, wherein X₁ is Q or H, and X₂ is
T or H, (SEQ ID NO: 41)
X₁X₂X₃X₄RAPYX₅, wherein X₁ is Q or H, X2 is R or
H, X3 is Y or H, X4 is N or H, and X₅ is T or H,
wherein at least X₁ or X₂ or X₃ or X₄ or X₅ is H.
```

The invention further provides mutated adalimumab or antigen binding fragment thereof comprising a CDR1 light chain sequence selected from the group consisting of:

```
                                      (SEQ ID NO: 15)
RASQGIRNHLA, (SEQ ID NO: 16)
RASQGIRNHHA, (SEQ ID NO: 42)
RASQGIRNX₁X₂A, wherein X₁ is Y or H, X₂ is L or
H, wherein at least X₁ or X₂ is H.
```

The invention further provides mutated adalimumab or antigen binding fragment thereof comprising a CDR2 light chain sequence selected from the group consisting of:

```
                                      (SEQ ID NO: 32)
         AAHTLQS
```

In an embodiment of the invention, the histidine-mutated adalimumab or antigen binding fragment thereof comprises a CDR3 heavy chain sequence as specified above and in the claims, and a CDR1 light chain sequence as specified above and in the claims.

In a further embodiment of the invention, the histidine-mutated adalimumab or antigen binding fragment thereof comprises a CDR3 heavy chain sequence, and a CDR3 light chain sequence as specified above and in the claims.

In a further embodiment of the invention, the histidine-mutated adalimumab or antigen binding fragment thereof comprises a CDR3 heavy chain sequence, a CDR2 light chain sequence, and a CDR3 light chain sequence as specified above and in the claims.

In another embodiment of the invention, the histidine-mutated adalimumab or antigen binding fragment thereof comprises a CDR3 heavy chain sequence, a CDR1 light chain sequence, and a CDR3 light chain sequence as specified above and in the claims.

It was found by the inventors that preferable versions of histidine-mutated adalimumab comprise one of the following light chain variable regions:

```
(i)
                                      (SEQ ID NO: 28)
DIQMTQSPSS LSASVGDRVT ITCRASQGIR NHHAWYQQKP
GKAPKLLIYA ASTLQSGVPS RFSGSGSGTD FTLTISSLQP
EDVATYYCQR YNRAPYTFGQ GTKVEIK (ii)
                                      (SEQ ID NO: 29)
DIQMTQSPSS LSASVGDRVT ITCRASQGIR NYLAWYQQKP
GKAPKLLIYA ASTLQSGVPS RFSGSGSGTD FTLTISSLQP
EDVATYYCHH YHRAPYTFGQ GTKVEIK.

(iii)
                                      (SEQ ID NO: 30)
DIQMTQSPSS LSASVGDRVT ITCRASQGIR NYLAWYQQKP
GKAPKLLIYA ASTLQSGVPS RFSGSGSGTD FTLTISSLQP
EDVATYYCQH YHRAPYHFGQ GTKVEIK.

(iv)
                                      (SEQ ID NO: 33)
DIQMTQSPSS LSASVGDRVT ITCRASQGIR NYLAWYQQKP
GKAPKLLIYA ASTLQSGVPS RFSGSGSGTD FTLTISSLQP
EDVATYYCQH YHRAPYTFGQ GTKVEIK.

(v)
                                      (SEQ ID NO: 34)
DIQMTQSPSS LSASVGDRVT ITCRASQGIR NHLAWYQQKP
GKAPKLLIYA ASTLQSGVPS RFSGSGSGTD FTLTISSLQP
EDVATYYCQR YNHAPYTFGQ GTKVEIK (vi)
                                      (SEQ ID NO: 35)
DIQMTQSPSS LSASVGDRVT ITCRASQGIR NHLAWYQQKP
GKAPKLLIYA ASTLQSGVPS RFSGSGSGTD FTLTISSLQP
EDVATYYCQR YNRAPYTFGQ GTKVEIK (vii)
                                      (SEQ ID NO: 36)
DIQMTQSPSS LSASVGDRVT ITCRASQGIR NYLAWYQQKP
GKAPKLLIYA ASTLQSGVPS RFSGSGSGTD FTLTISSLQP
EDVATYYCQR HNRAPYTFGQ GTKVEIK (viii)
                                      (SEQ ID NO: 37)
DIQMTQSPSS LSASVGDRVT ITCRASQGIR NHLAWYQQKP
GKAPKLLIYA AHTLQSGVPS RFSGSGSGTD FTLTISSLQP
EDVATYYCQR YNRAPYTFGQ GTKVEIK (ix)
                                      (SEQ ID NO: 20)
DIQMTQSPSS LSASVGDRVT ITCRASQGIR NHX₁AWYQQKP
GKAPKLLIYA ASTLQSGVPS RFSGSGSGTD FTLTISSLQP
EDVATYYCQR YNRAPYTFGQ GTKVEIK,
wherein X₁ is L or H,
```

(x)
```
                                            (SEQ ID NO: 21)
DIQMTQSPSS LSASVGDRVT ITCRASQGIR NYLAWYQQKP
GKAPKLLIYA ASTLQSGVPS RFSGSGSGTD FTLTISSLQP
EDVATYYCX₁H YHRAPYX₂FGQ GTKVEIK, wherein X₁
is Q or H and X₂ is T or H
```

(xi)
```
                                            (SEQ ID NO: 22)
DIQMTQSPSS LSASVGDRVT ITCRASQGIR NYLAWYQQKP
GKAPKLLIYA ASTLQSGVPS RFSGSGSGTD FTLTISSLQP
EDVATYYCHH YHRAPYX₁FGQ GTKVEIK, wherein X₁ is T
or H,
```

(xii)
```
                                            (SEQ ID NO: 23)
DIQMTQSPSS LSASVGDRVT ITCRASQGIR NYLAWYQQKP
GKAPKLLIYA ASTLQSGVPS RFSGSGSGTD FTLTISSLQP
EDVATYYCX₁H YHRAPYHFGQ GTKVEIK, wherein X₁ is
Q or H;
```

(xiii)
```
                                            (SEQ ID NO: 24)
DIQMTQSPSS LSASVGDRVT ITCRASQGIR NHX₁AWYQQKP
GKAPKLLIYA ASTLQSGVPS RFSGSGSGTD FTLTISSLQP
EDVATYYCX₂H YHRAPYX₃FGQ GTKVEIK, wherein X₁ is
L or H, and X₂ is Q or H and X₃ is T or H;
```

(xiv)
```
                                            (SEQ ID NO: 43)
DIQMTQSPSS LSASVGDRVT ITCRASQGIR NX₁X₂AWYQQKP
GKAPKLLIYA AX₃TLQSGVPS RFSGSGSGTD FTLTISSLQP
EDVATYYCX₄X₅ X₆X₇RAPYX₈FGQ GTKVEIK, wherein X₁ is Y
or H, X₂ is L or H, X₃ is S or H, X₄ is Q or H,
X₅ is R or H, X₆ is Y or H, X₇ is N or H, X₈ is T or
H, wherein at least X₁ or X₂ or X₃ or X₄ or X₅ or
X₆ or X₇ or X₈ is H.
```

It was further found by the inventors that preferable versions of histidine-mutated adalimumab comprise one of the following heavy chain variable regions:

(i)
```
                                            (SEQ ID NO: 25)
EVQLVESGGG LVQPGRSLRL SCAASGFTFD DYAMHWVRQA
PGKGLEWVSA ITWNSGHIDY ADSVEGRFTI SRDNAKNSLY
LQMNSLRAED TAVYYCAKVS YHSTASSLDY WGQGTLVTVS S;
```

(ii)
```
                                            (SEQ ID NO: 26)
EVQLVESGGG LVQPGRSLRL SCAASGFTFD DYAMHWVRQA
PGKGLEWVSA ITWNSGHIDY ADSVEGRFTI SRDNAKNSLY
LQMNSLRAED TAVYYCAKVS YLSTAHHLDY WGQGTLVTVS S;
```

(iii)
```
                                            (SEQ ID NO: 39)
EVQLVESGGG LVQPGRSLRL SCAASGFTFD DYAMHWVRQA
PGKGLEWVSA ITWNSGHIDY ADSVEGRFTI SRDNAKNSLY
LQMNSLRAED TAVYYCAKVH YHSTASSLDY WGQGTLVTVS S,
```

(iv)
```
                                            (SEQ ID NO: 44)
EVQLVESGGG LVQPGRSLRL SCAASGFTFD DYAMHWVRQA
PGKGLEWVSA ITWNSGHIDY ADSVEGRFTI SRDNAKNSLY
LQMNSLRAED TAVYYCAKVX₁ YX₂STAX₃X₄LDY WGQGTLVTVS S,
wherein X₁ is S or H, X₂ is L or H, X₃ is S or H,
X₄ is S or H, wherein at least X₁ or X₂ or X₃ or
X₄ is H.
```

Preferable histidine-mutated adalimumab according to the invention comprises any of the variable light chains as specified above and any one of the variable heavy chain domains as specified above.

A first preferred embodiment of the invention is a respectively histidine-mutated adalimumab comprising the variable heavy chain sequence:

```
                                            (SEQ ID NO: 5)
EVQLVESGGG LVQPGRSLRL SCAASGFTFD DYAMHWVRQA
PGKGLEWVSA ITWNSGHIDY ADSVEGRFTI SRDNAKNSLY
LQMNSLRAED TAVYYCAKVS YHSTASSLDY WGQGTLVTVS S
``` and the variable light chain sequence:

```
                                            (SEQ ID NO: 27)
DIQMTQSPSS LSASVGDRVT ITCRASQGIR NHHAWYQQKP
GKAPKLLIYA ASTLQSGVPS RFSGSGSGTD FTLTISSLQP
EDVATYYCQR YNRAPYTFGQ GTKVEIK
```

A second preferred embodiment of the invention is a respectively histidine-mutated adalimumab comprising the variable heavy chain sequence:

```
                                            (SEQ ID NO: 26)
EVQLVESGGG LVQPGRSLRL SCAASGFTFD DYAMHWVRQA
PGKGLEWVSA ITWNSGHIDY ADSVEGRFTI SRDNAKNSLY
LQMNSLRAED TAVYYCAKVS YLSTAHHLDY WGQGTLVTVS S
``` and the variable light chain sequence:

```
                                            (SEQ ID NO: 28)
DIQMTQSPSS LSASVGDRVT ITCRASQGIR NYLAWYQQKP
GKAPKLLIYA ASTLQSGVPS RFSGSGSGTD FTLTISSLQP
EDVATYYCHH YHRAPYTFGQ GTKVEIK.
```

A third preferred embodiment of the invention is a respectively histidine-mutated adalimumab comprising the variable heavy chain sequence:

```
                                            (SEQ ID NO: 26)
EVQLVESGGG LVQPGRSLRL SCAASGFTFD DYAMHWVRQA
PGKGLEWVSA ITWNSGHIDY ADSVEGRFTI SRDNAKNSLY
LQMNSLRAED TAVYYCAKVS YLSTAHHLDY WGQGTLVTVS S
``` and the variable light chain sequence:

```
                                            (SEQ ID NO: 29)
DIQMTQSPSS LSASVGDRVT ITCRASQGIR NYLAWYQQKP
GKAPKLLIYA ASTLQSGVPS RFSGSGSGTD FTLTISSLQP
EDVATYYCQH YHRAPYHFGQ GTKVEIK
```

The histidine-mutated adalimumab antibodies or variants or fragments thereof can further comprise human heavy and/or light constant regions.

In one embodiment they comprise a human IgG, preferably a human IgG1 (such as specified by SEQ ID NO: 11), or IgG2 heavy chain constant region.

In another embodiment of the invention they comprise human kappa light chain constant region.

In another embodiment of the invention, the histidine-mutated adalimumab versions of the invention comprise a human heavy chain constant region, preferably IgG1, wherein the Fc portion is mutated at one or more amino acid positions by replacement of the original amino acid residues by other natural amino acid residues which mediate (increase or decrease) binding of the antibody to FcRn.

The histidine-mutated adalimumab antibodies of the invention can be conjugated to other molecules by recombinant fusion with other polypeptides or proteins such as cytokine, or by chemical linkage to chemical, preferably cytotoxic entities, preferably via linker molecules to form antibody-drug-conjugates (ADCs). Techniques and methods to produce such antibody fusion proteins or antibody drug conjugates are well established in the art.

The invention also provides pharmaceutical compositions suitable for the treatment of inflammatory, autoimmune or cancer diseases comprising histidine-mutated anti-TNFα antibody adalimumab or a variant or an antigen binding fragment thereof, or a respective antibody-drug conjugate or an antibody cytokine fusion protein together with a pharmaceutically acceptable carrier, diluent or excipient.

The invention finally provides the therapeutic use of such histidine-mutated adalimumab or biologically effective and active variant or fragment thereof, or ADCs or fusion proteins thereof, for the manufacture of a medicament for the treatment of TNFα induced inflammatory, autoimmune or cancer diseases, as specified in detail below.

The histidine-mutated adalimumab versions of the inventions exhibit the following advantageous properties and functions:

- Adalimumab binding sites are no longer blocked over a long period of time upon TNFα-binding.
- Adalimumab shows significantly improved pH-sensitive binding to the target antigen.
- The sTNFα can be released much more efficiently by histidine-mutated adalimumab in the acidified endosome during recycling via FcRn.
- Upon binding to the membrane-bound target (mTNFα) initiation of receptor mediated internalization and lysosomal degradation of the mTNFα-adalimumab complex which would lead to elimination of the antibody, can be avoided or reduced.
- Improved pharmacokinetics of the TNFα-binding antibody that exhibit pH-dependent target binding
- pH-sensitive antibody variants are derived from the parental adalimumab sequence by altering the amino-acid sequences within the variable regions of the antibody.
- Incorporation of pH-sensitivity into adalimumab is established by substitutions of aminoacids of the heavy and light chain variable regions with histidines
- The pH-sensitivity of adalimumab variants corresponds to increased ratios between kinetic parameters (KD, kdis) at pH 6/pH 7.4 in comparison to the ratios of parental adalimumab.
- In this regard the adalimumab antibodies according to the invention are enabled to neutralize the antigen multiple times
- Therefore, the therapeutic effect may be prolonged and may allow less frequent administrations of the antibody and/or administrations at lower doses.

DETAILS OF THE INVENTION

Tumor Necrosis Factor α (TNFα):

TNFα is a cytokine that plays a key role in immune responses by initiating defense responses to e.g. some bacterial infections. It acts in a complex network in normal inflammation and is also involved in lymphoid tissue development (Tracey et al., 2008).

Many different cells produce TNFα including macrophages, T cells, mast cells and granulocytes, to name a few. TNFα is a general term that includes soluble (sTNFα) and transmembrane TNFα (mTNFα). Soluble homotrimers are released by cells after proteolytic cleavage of transmembrane TNFα (homotrimers of 26 kDa monomers) by the metalloprotease TNF-alpha-converting enzyme (TACE) (Wajant et al., 2003). Both forms, the sTNFα or mTNFα interact with two distinct receptors, TNF receptor 1 (TNFR1) and TNF receptor 2 (TNFR2). Both receptors differ in their cellular expression profiles and signaling mechanisms. Complexity of the interaction network increases as mTNFα itself can act either as ligand or receptor to both TNF receptors (Wajant et al., 2003).

During disease, high expression of TNFα triggers and mediates downstream mechanisms that can lead to chronic inflammation and pathogenesis within affected compartments (Tracey et al., 2008). Common consequences of TNFα activities in autoimmune diseases are modulation of immune cell recruitment, cell proliferation, cell death and immune regulation. Other effects like matrix degradation and osteoclastogenesis are more disease specific and may be related to different cell types in the affected tissues (Reviewed in Tracey et al., 2008, Choy & Panayi, 2001; Feldmann, 2002; Schottelius et al., 2004).

TNFα has a particularly important role in the regulation of pathogenic events in e.g. rheumatoid arthritis, crohn's disease and plaque psoriasis and rapidly induces other cytokines (e.g. IL-1β and IL-6) (Tracey et al., 2008). In several inflammatory autoimmune diseases the positive clinical outcome upon TNFα-blockade by therapeutic anti-TNFα antibodies has corroborated the link between excessive TNFα exposition and disease pathologies (Aggawal, 2003; Tracey et al., 2008).

Adalimumab:

Adalimumab (also known by its trademark name HUMIRA®) is a fully human 148 kDa IgG1K monoclonal antibody against TNFα that originally was developed by using phage display (Abbott Laboratories, 2014). Since market launch in 2002, adalimumab generated huge sales that achieved $4.6 billion just on the US market in 2012 (Aggarwal, 2014). Adalimumab binds to TNFα with high sub-nanomolar affinity and thereby blocks the interaction between TNFα and p55 and p75 cell surface receptors TNFR1 or TNFR2 (Abbott Laboratories, 2014).

As adalimumab binds also to mTNFα with high affinity further possible modes of action include apoptosis or cytokine suppression upon reverse signaling mechanisms and CDC or ADCC mediated cell killing (Reviewed in Tracey et al., 2008 and Horiuchi et al, 2010).

The amino acid sequences of Adalimumab (and variants thereof) and its pharmacological and therapeutic properties are disclosed, for example in WO 97/029131.

The sequences which are important in view of the present invention are listed below in detail:

Adalimumab Full Light Chain Sequence:

(SEQ ID NO: 1)
DIQMTQSPSS LSASVGDRVT ITCRASQGIR NYLAWYQQKP
GKAPKLLIYA ASTLQSGVPS RFSGSGSGTD FTLTISSLQP
EDVATYYCQR YNRAPYTFGQ GTKVEIKRTV AAPSVFIFPP
SDEQLKSGTA SVVCLLNNFY PREAKVQWKV DNALQSGNSQ
ESVTEQDSKD STYSLSSTLT LSKADYEKHK VYACEVTHQG
LSSPVTKSFN RGEC

Adalimumab Light Chain Sequence, Variable Region (VL):

(SEQ ID NO: 2)
DIQMTQSPSS LSASVGDRVT ITCRASQGIR NYLAWYQQKP
GKAPKLLIYA ASTLQSGVPS RFSGSGSGTD FTLTISSLQP
EDVATYYCQR YNRAPYTFGQ GTKVEIK

Adalimumab CDR1 Sequence of VL

```
                                            (SEQ ID NO: 3)
         RASQGIRNYLA
```

Adalimumab CDR2 Sequence of VL

```
                                            (SEQ ID NO: 4)
         AASTLQS
```

Adalimumab CDR3 Sequence of VL

```
                                            (SEQ ID NO: 5)
         QRYNRAPYT
```

Adalimumab Full Heavy Chain Sequence:

```
                                            (SEQ ID NO: 6)
    EVQLVESGGG LVQPGRSLRL SCAASGFTFD DYAMHWVRQA
    PGKGLEWVSA ITWNSGHIDY ADSVEGRFTI SRDNAKNSLY
    LQMNSLRAED TAVYYCAKVS YLSTASSLDY WGQGTLVTVS
    SASTKGPSVF PLAPSSKSTS GGTAALGCLV KDYFPEPVTV
    SWNSGALTSG VHTFPAVLQS SGLYSLSSVV TVPSSSLGTQ
    TYICNVNHKP SNTKVDKKVE PKSCDKTHTC PPCPAPELLG
    GPSVFLFPPK PKDTLMISRT PEVTCVVVDV SHEDPEVKFN
    WYVDGVEVHN AKTKPREEQY NSTYRVVSVL TVLHQDWLNG
    KEYKCKVSNK ALPAPIEKTI SKAKGQPREP QVYTLPPSRD
    ELTKNQVSLT CLVKGFYPSD IAVEWESNGQ PENNYKTTPP
    VLDSDGSFFL YSKLTVDKSR WQQGNVFSCS VMHEALHNHY
    TQKSLSLSPG K
```

Adalimumab Heavy Chain Sequence, Variable Region (VH):

```
                                            (SEQ ID NO: 7)
    EVQLVESGGG LVQPGRSLRL SCAASGFTFD DYAMHWVRQA
    PGKGLEWVSA ITWNSGHIDY ADSVEGRFTI SRDNAKNSLY
    LQMNSLRAED TAVYYCAKVS YLSTASSLDY WGQGTLVTVS S
```

Adalimumab CDR1 Sequence of VH:

```
                                            (SEQ ID NO: 8)
         DYAMH
```

Adalimumab CDR2 Sequence of VH:

```
                                            (SEQ ID NO: 9)
         AITWNSGHIDYADSVEG
```

Adalimumab CDR3 Sequence of VH:

```
                                            (SEQ ID NO: 10)
         VSYLSTASSLDY
```

Adalimumab Human Heavy Chain IgG1 Constant Region:

```
                                            (SEQ ID NO: 11)
    ASTKGPSVF PLAPSSKSTS GGTAALGCLV KDYFPEPVTV
    SWNSGALTSG VHTFPAVLQS SGLYSLSSVV TVPSSSLGTQ
    TYICNVNHKP SNTKVDKKVE PKSCDKTHTC PPCPAPELLG
    GPSVFLFPPK PKDTLMISRT PEVTCVVVDV SHEDPEVKFN
    WYVDGVEVHN AKTKPREEQY NSTYRVVSVL TVLHQDWLNG
    KEYKCKVSNK ALPAPIEKTI SKAKGQPREP QVYTLPPSRD
    ELTKNQVSLT CLVKGFYPSD IAVEWESNGQ PENNYKTTPP
    VLDSDGSFFL YSKLTVDKSR WQQGNVFSCS VMHEALHNHY
    TQKSLSLSPG K
```

Adalimumab is approved in many countries for a couple of therapeutic treatments, such as rheumatoid arthritis, psoriatic arthritis, ankylosing spondylitis, and Crohn's disease.

Therefore, the histidine-mutated adalimumab versions according to the invention are also applicable in the treatment of rheumatoid arthritis, psoriatic arthritis, ankylosing spondylitis, and Crohn's disease, but also in the treatment of other diseases which are induced or triggered by TNFα. This may include autoimmune disorders as well as cancer diseases.

Selection of Antibodies:

Selection of suitable anti-TNFα antibody versions of adalimumab and fragments thereof according to the invention may be achieved by well established and known methods and techniques in the art, such as by histidine substitution via page display libraries or from combinatorial histidine substitution libraries by yeast surface display. Details are provided in the Example section.

Terms, Definitions, Details

The term "antibody" or "immunoglobulin" is used according to the invention in the broadest sense and specifically covers intact monoclonal antibodies, polyclonal antibodies, multispecific antibodies (e.g. bispecific antibodies) formed from at least two intact antibodies, and antibody fragments, so long as they exhibit the desired biological activity. Depending on the amino acid sequence of their constant regions, intact or whole antibodies can be assigned to different classes. There are five major classes of intact antibodies: IgA, IgD, IgE, IgG, and IgM, and several of these may be further divided into "subclasses" (isotypes), e.g., IgG1, IgG2, IgG3, IgG4, IgA, and IgA2.

Preferred major class for antibodies according to the invention is IgG, in more detail IgG1 and IgG2, most preferably IgG1.

"Antibody fragments" according to the invention comprise a portion of an intact antibody, preferably comprising the antigen-binding or variable region thereof. Examples of antibody fragments include Fab, Fab', F(ab')2, Fv and Fc fragments, diabodies, linear antibodies, single-chain antibody molecules; bispecific and multispecific antibodies formed from antibody fragment(s).

A "whole or complete" antibody according to the invention is an antibody which comprises an antigen-binding variable region as well as a light chain constant domain (CL) and heavy chain constant domains, CH1, CH2 and CH3.

A "Fc" region of an antibody according to the invention comprises, as a rule, a CH2, CH3 and the hinge region of an IgG1 or IgG2 antibody major class. The hinge region is a group of about 15 amino acid residues which combine the CH1 region with the CH2-CH3 region.

A "Fab" fragment also contains the constant domain of the light chain and the first constant domain (CH1) of the heavy chain and has one antigen-binding site only.

A "Fab'" fragments differ from Fab fragments by the addition of a few residues at the carboxy-terminus of the heavy chain CH1 domain including one or more cysteine residues from the antibody hinge region.

A "F(ab')2" antibody according to this invention is produced as pairs of Fab' fragments which have hinge cysteines between them.

"Single-chain FV" or "scFv" antibody fragments according to the invention comprise the $V_H$ and $V_L$ domains of antibody, wherein these domains are present in a single polypeptide chain. Preferably, the Fv polypeptide further comprises a polypeptide linker between the VH and VL domains which enables the scFv to form the desired structure for antigen binding.

The "variable domain" of an antibody according to the invention comprises the framework regions (usually FR1 to FR4) as well as the CDR domains (usually CDR1, CDR2 and CDR3) which are designated as "hypervariable regions".

The term "hypervariable region" or "CDR" when used herein refers to the amino acid residues of an antibody which are responsible for antigen-binding. The hypervariable region generally comprises amino acid residues from a "complementarity determining region" or "CDR" (e.g. residues 24-34 (L1), 50-56 (L2) and 89-97 (L3) in the light chain variable domain and 31-35 (H1), 50-65 (H2) and 95-102 (H3) in the heavy chain variable domain; and/or those residues from a "hypervariable loop" (e.g. residues 26-32 (L1), 50-52 (L2) and 91-96 (L3) in the light chain variable domain and 26-32 (H1), 53-55 (H2) and 96-101 (H3) in the heavy chain variable domain; Chothia and Lesk *J. Mol. Biol.* 196:901-917 (1987)).

If not otherwise pointed out, the amino acid positions within the antibody molecules according to this invention are numbered according to Kabat.

"Framework Region" or "FR" residues are those variable domain residues other than the hypervariable region residues as herein defined.

"Antibody variants" according to the invention include antibodies that have a modified amino acid sequence compared to the parental antibody but have same or changed binding affinity to the targeted antigen. Antibody variants differ from the parental antibody by replacement or deletion or addition of one or more amino acid residues at specific positions within the variable domains, including the CDR domains, and or the constant regions of the antibody, in order to modify certain properties of the antibody, such as binding affinity and/or receptor functions, like ADCC, FcRn binding and the more. The histidine-mutated antibodies of this invention without further modifications are not designated as "antibody variants" according to this invention. Antibody variants according to the invention exhibit a sequence homology of 80-99% compared to the parental antibody, preferably 90%, 91%, 92%, 93%, 94%, 95%, 96%, 97%, 98% and 99%, dependent on the specific location of the amino acid residue to be replaced, deleted or added.

The term "fusion protein" refers to a natural or synthetic molecule consisting of one ore more biological molecules as defined above, wherein two or more peptide- or protein-based (glycoproteins included) molecules having different specificity are fused together optionally by chemical or amino acid based linker molecules. The linkage may be achieved by C—N fusion or N—C fusion (in 5'→3' direction), preferably C—N fusion. A fusion protein according to the invention is said fusion of an antibody or antibody variant of this invention fused to another protein or polypeptide, preferably a cytokine.

The term "antibody-drug conjugate (ADC)" refers according to the invention to an immunoconjugate composed of an antibody, preferably complete antibody, according to the invention, and a preferably chemical cytotoxic agent. The components are chemically attached to each other by specific linkers. The antibody of the invention (preferably within its heavy chain constant region) may be modified at one or more amino acid positions in order to create a suitable linkage to the linker and/or the cytotoxic payload drug. Method and techniques to generate such ADCs are well known in the art.

The term "Fc receptor" means, according to the invention, receptors for the Fc region of immunoglobulins (FcRs) that link humoral responses to cellular activities within the immune system. Based on their function, two general groups of FcR can be distinguished: those expressed predominantly by leucocytes that trigger antibody effector functions and those that primarily mediate transport of immunoglobulins across epithelial or endothelial surfaces. ADCC is triggered through interaction of target-bound antibodies (belonging to IgG or IgA or IgE classes) with certain Fc receptors (FcRs). ADCC involving human IgG1 is highly dependent on the glycosylation profile of its Fc portion and on the polymorphism of Fcγ receptors. The term "FcRn" means the specific neonatal Fc receptor, which binds binds IgG at acidic pH of (<6.5) but not at neutral or higher pH. The receptor is responsible for extending half-life of IgG antibodies in serum.

The term "cytokine" is a generic term for proteins released by one cell population which act on another cell as intercellular mediators. Examples of such cytokines are lymphokines, monokines, and traditional polypeptide hormones, such as vascular endothelial growth factor (VEGF); integrin; thrombopoietin (TPO); nerve growth factors such as NGFβ; platelet-growth factor; transforming growth factors (TGFs) such as TGFα and TGFβ; erythropoietin (EPO); interferons such as IFNα, IFNβ, and IFNγ; colony stimulating factors such as M-CSF, GM-CSF and G-CSF; interleukins such as IL-1, IL-1a, IL-2, IL-3, IL-4, IL-5, IL-6, IL-7, IL-8, IL-9, IL-10, IL-11, IL-12; and TNF-α or TNF-β.

The term "biologically/functionally effective" or "therapeutically effective (amount)" refers to a drug/molecule which causes a biological function or a change of a biological function in vivo or in vitro, and which is effective in a specific amount to treat a disease or disorder in a mammal, preferably in a human.

The term "pharmaceutical treatment" means a variety of modalities for practicing the invention in terms of the steps. For example, the agents according to the invention can be administered simultaneously, sequentially, or separately. Furthermore, the agents can be separately administered within one or more time intervals between administrations. Therapeutic compositions of the present invention contain a physiologically tolerable carrier together with the relevant agent as described herein, dissolved or dispersed therein as an active ingredient.

As used herein, the term "pharmaceutically acceptable" refers to compositions, carriers, diluents and reagents which represent materials that are capable of administration to or upon a mammal without the production of undesirable physiological effects such as nausea, dizziness, gastric upset and the like. The preparation of a pharmacological composition that contains active ingredients dissolved or dispersed therein is well understood in the art and need not be limited based on formulation. Typically, such compositions are prepared as injectable preparation either as liquid solutions or suspensions, however, solid forms suitable for solution, or suspensions, in liquid prior to use can also be prepared. The preparation can also be emulsified. The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which may enhance the effectiveness of the active ingredient. The therapeutic composition of the present invention can include pharmaceutically acceptable salts of the components therein.

The histidine-mutated adalimumab versions according to the invention are suitable for the treatment of the same disorders and diseases as the approved and marketed non-histidine mutated adalimumab (HUMIRA®), which are rheumatoid arthritis, juvenile idiopathic arthritis, psoriatic arthritis, ankylosing spondylitis, Crohn's disease, ulcerative colitis and chronic plaque psoriasis, wherein the drug is preferably administered by subcutaneous injection.

Like the marketed drug, the histidine-mutated adalimumab according to the invention can be used alone or in combination with other drugs which support the therapy, such as methotrexate, DMARDS, glucocorticoids, non-steroidal anti-inflammatory drugs (NSAIDs), and/or analgesics.

The standard dose regimen of HUMIRA® is usually 40 mg every week as single dose. The histidine-mutated adalimumab versions according exhibit, as pointed out earlier, a significantly stronger pH-dependency as HUMIRA®, and thus can be administered in doses which correspond only 10-90%, in detail 10%, 20%, 30%, 40%, 50%, 60%, 70%, 80% and 90%, of the recommended dose of HUMIRA®, dependent on the respective $K_{dis}$ values of the used histidine-mutated adalimumab versions.

SHORT DESCRIPTION OF THE FIGURES

FIG. 1: Proposed differences between a) conventional and b) pH-dependent antibody on soluble antigen binding (Modified from: Igawa et al., 2010).

Figure 2:
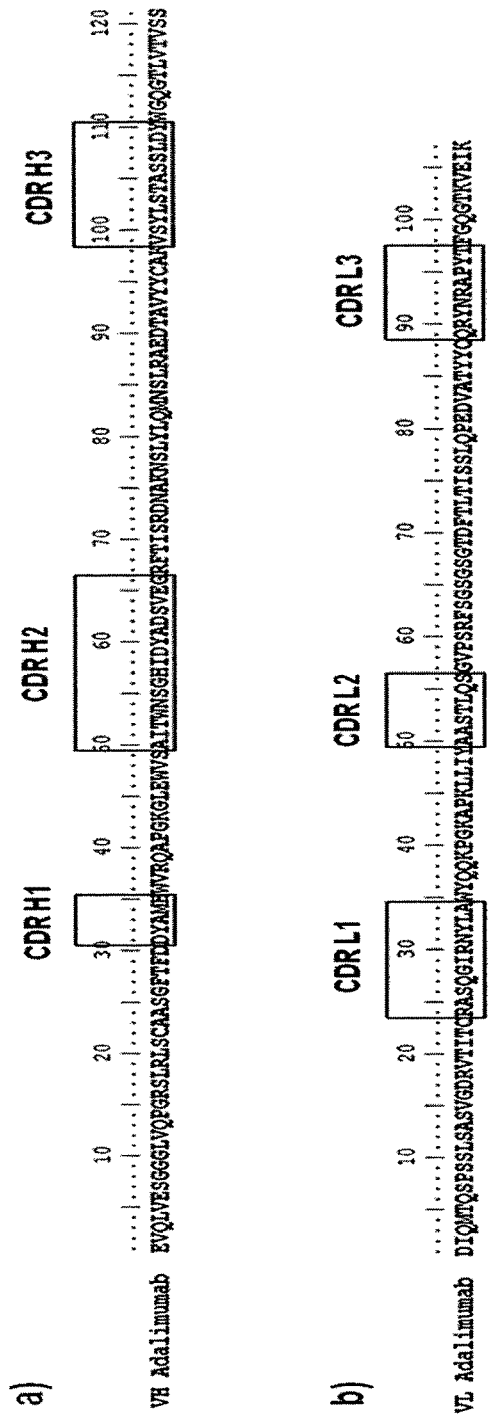

FIG. 2: Adalimumab amino acid sequences of the variable regions. The complementary determining regions are highlighted with red boxes. a) Variable region of the heavy chain (VH). b) Variable region of the light chain (VL).

Figure 3A:
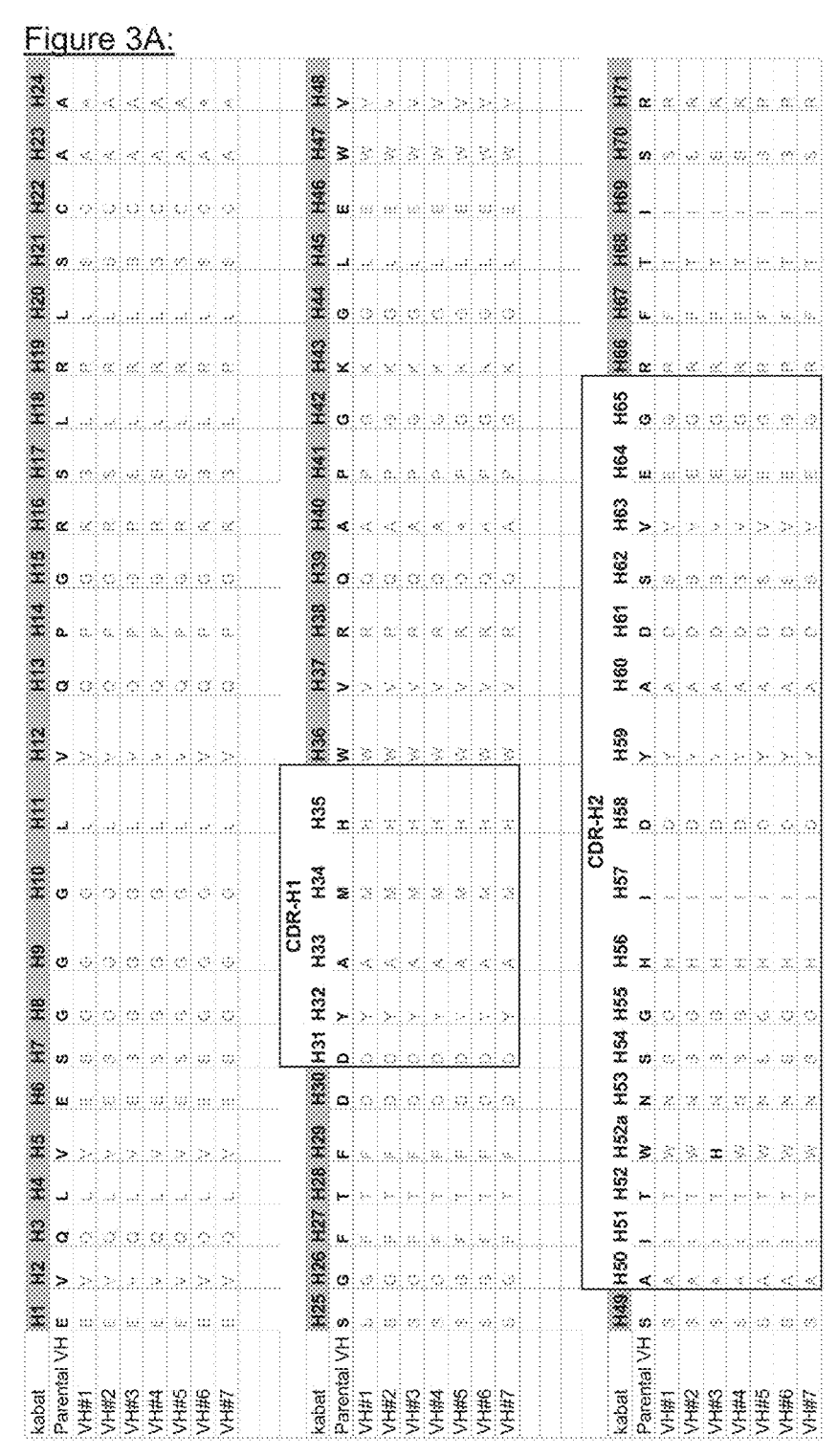

FIG. 3A: First part of aligned protein sequences of seven unique VH variants with the parental VH. Unique sequences were isolated from the heavy chain library approach after three rounds of screening. Parental VH sequence is shown on top and residues that vary from the parental VH are highlighted for every variant.

Figure 3B:
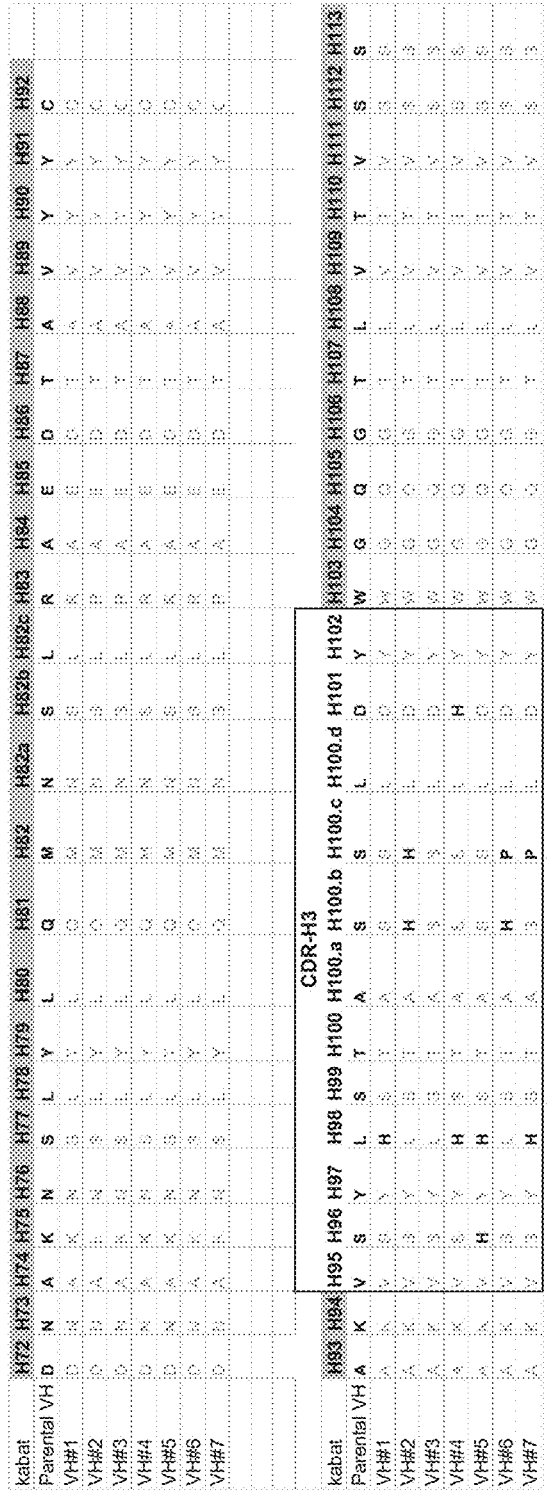

FIG. 3B: Second part of aligned protein sequences of seven unique VH variants with the parental VH. Unique sequences were isolated from the heavy chain library approach after three rounds of screening. Parental VH sequence is shown on top and residues that vary from the parental VH are highlighted for every variant.

Figure 4A:
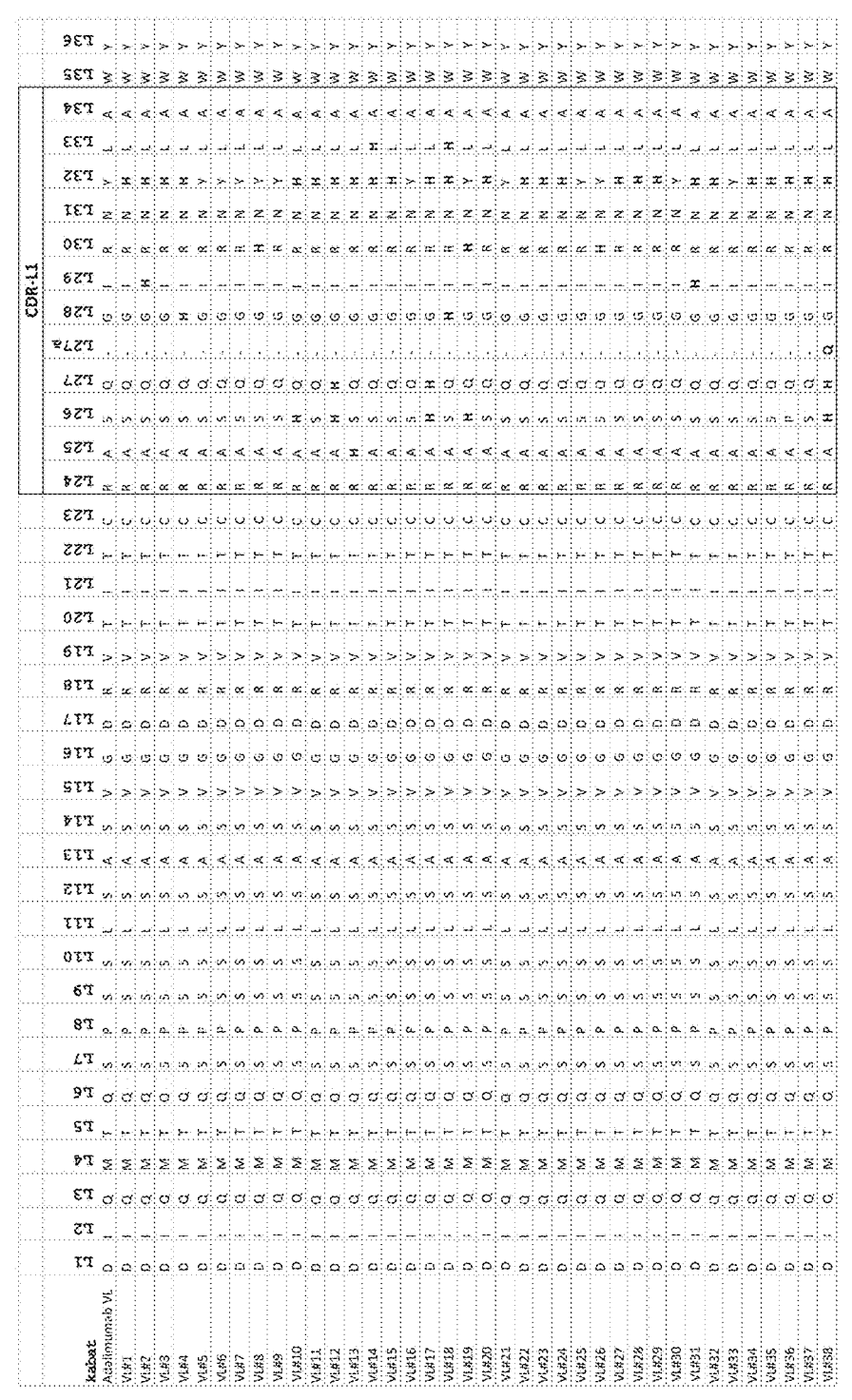

FIG. 4A: First part of protein sequence alignment (1-3 parts) of the parental VL and 38 unique VL variants that were isolated from the light chain library after three rounds of screening. Parental VL sequence is shown on top and residues that vary from the parental VL are highlighted for every variant.

Figure 4B:
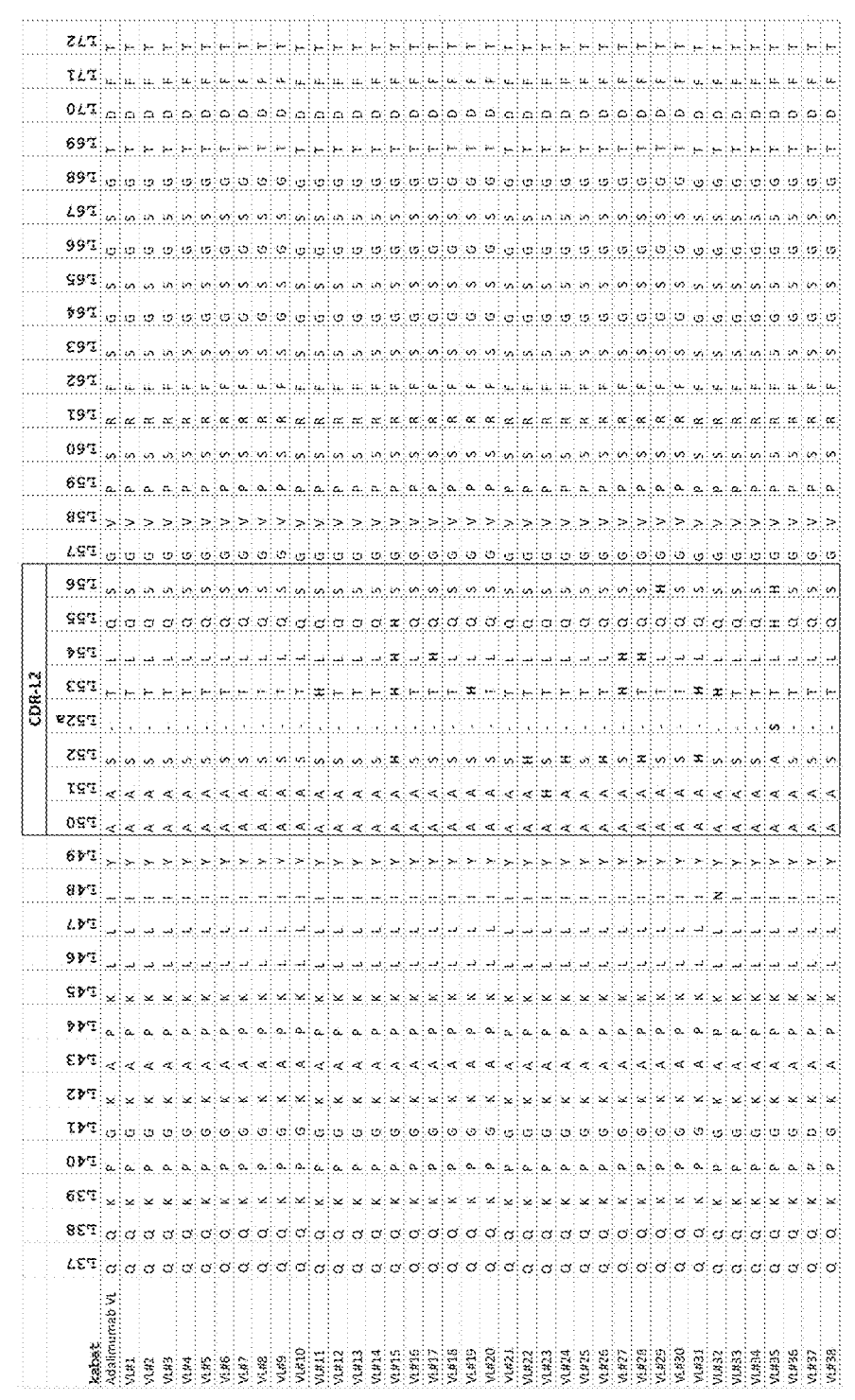

FIG. 4B: Second part of protein sequence alignment (1-3 parts) of the parental VL and 38 unique VL variants that were isolated from the light chain library after three rounds of screening. Parental VL sequence is shown on top and residues that vary from the parental VL are highlighted for every variant.

Figure 4C:
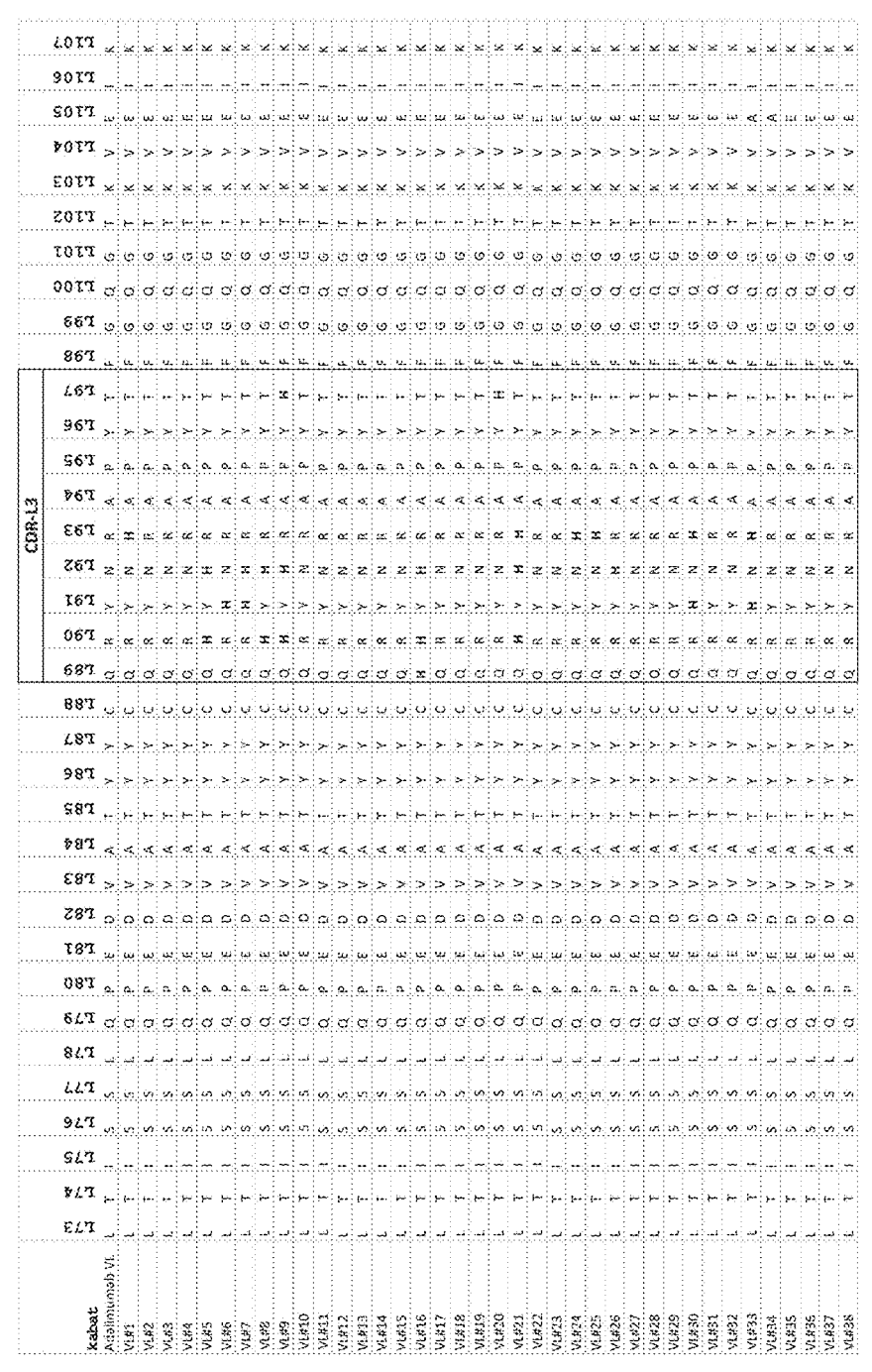

FIG. 4C: Third part of protein sequence alignment (1-3 parts) of the parental VL and 38 unique VL variants that were isolated from the light chain library after three rounds of screening. Parental VL sequence is shown on top and residues that vary from the parental VL are highlighted for every variant.

Figure 5:
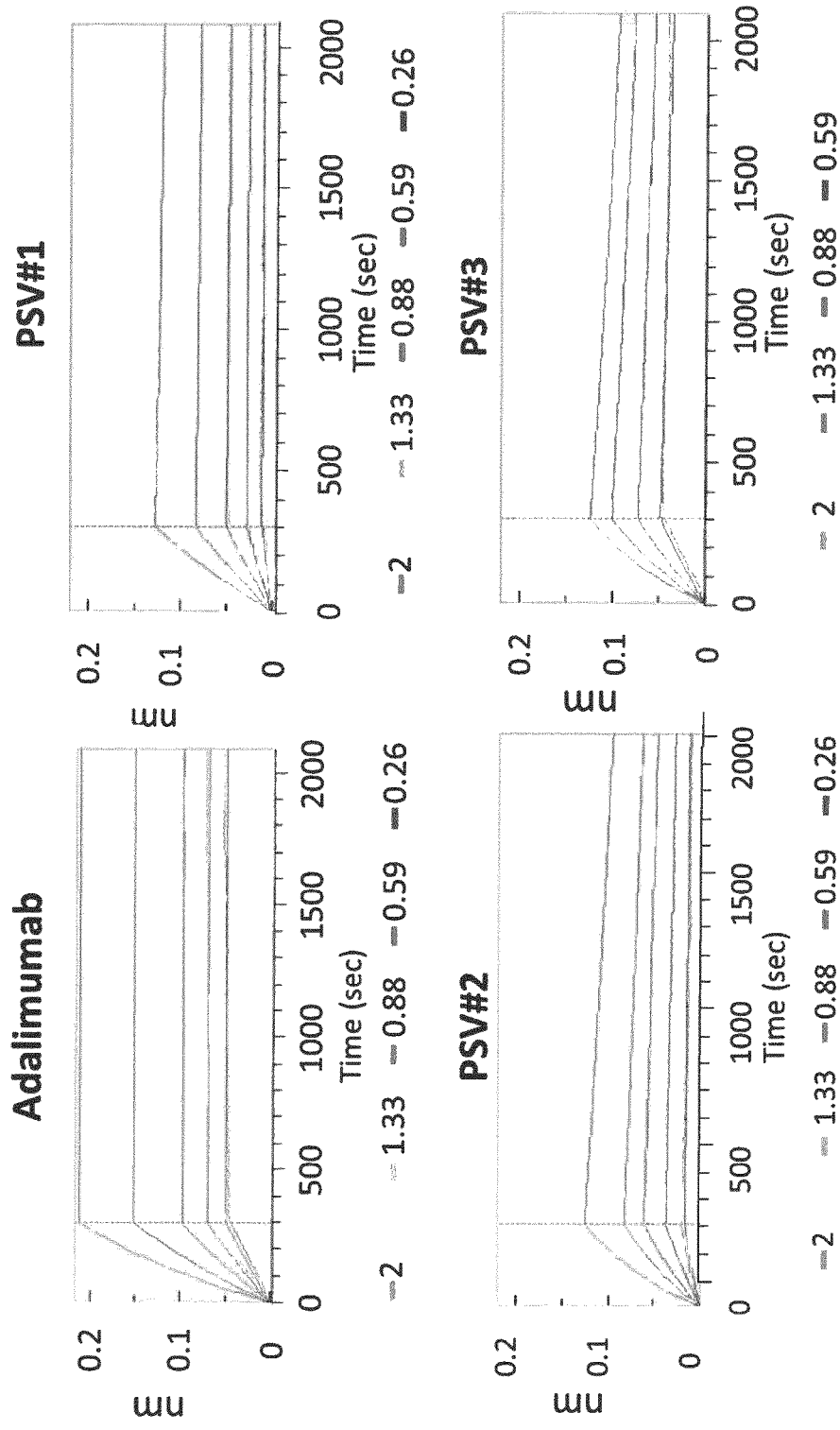

FIG. 5: Octet Red sensorgrams of adalimumab and three variants with pH-dependent binding to rhTNFα. Association was done with rhTNFα concentrations ranging between 0.26 nM-2 nM at pH 7.4 and dissociation was carried out at pH 7.4. Kinetics binding constants were determined through global fitting using Octet 8.0 Software.

Figure 6:
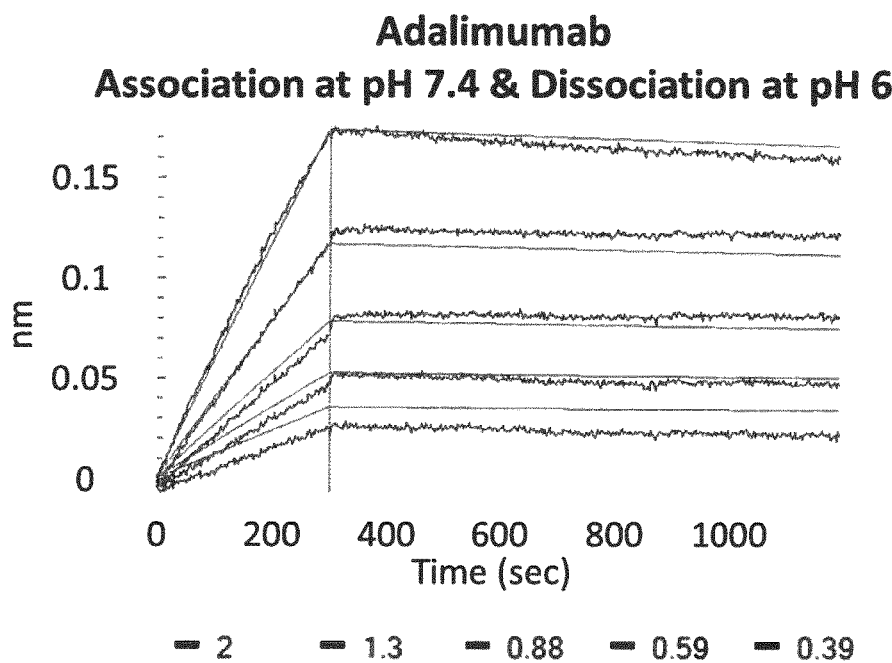
Figure 6:
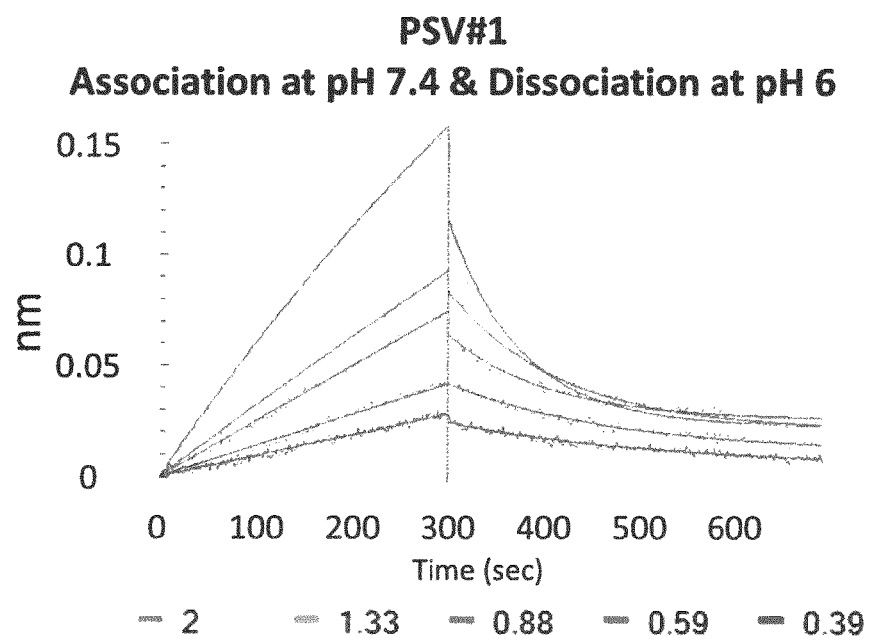
Figure 6:
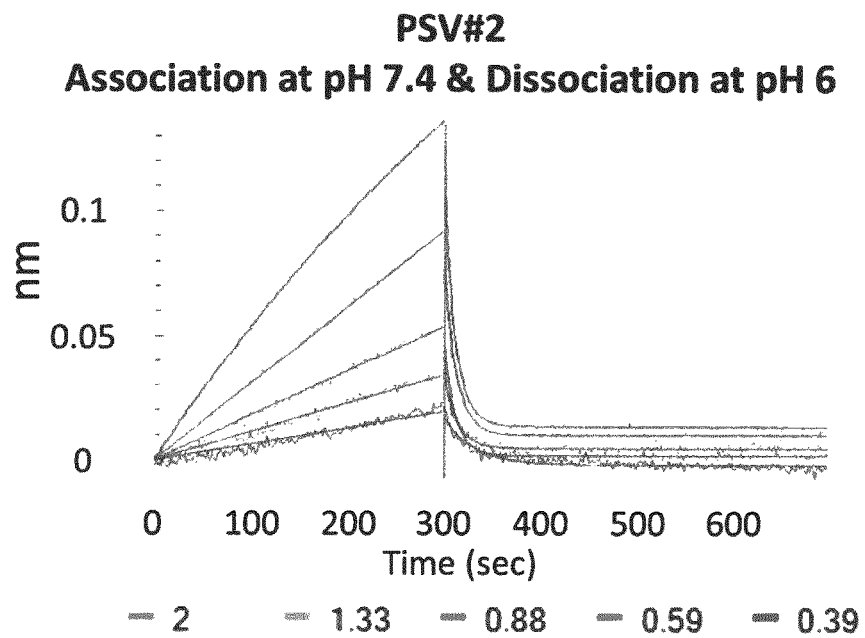
Figure 6:
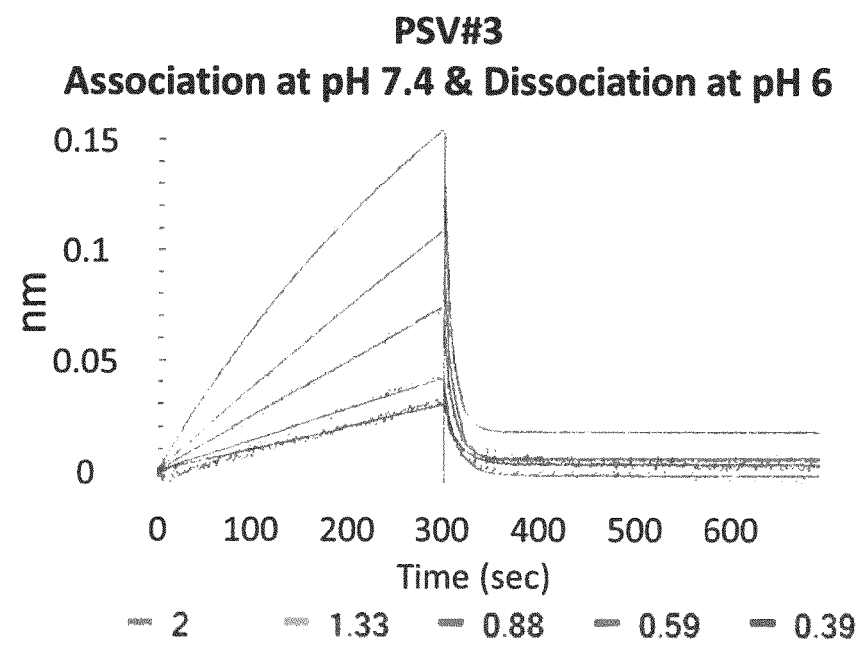

FIG. 6: Octet Red sensorgrams of adalimumab and three variants with pH-dependent binding. Association was done with rhTNFα concentrations ranging between 0.26 nM-2 nM at pH 7.4 and dissociation was carried out at pH 6. Off-rates were determined for PSV#1, PSV#2 and PSV#3 through local partial fitting using Octet 8.0 Software. Off-rates for adalimumab were generated by using global fitting.

Figure 7:
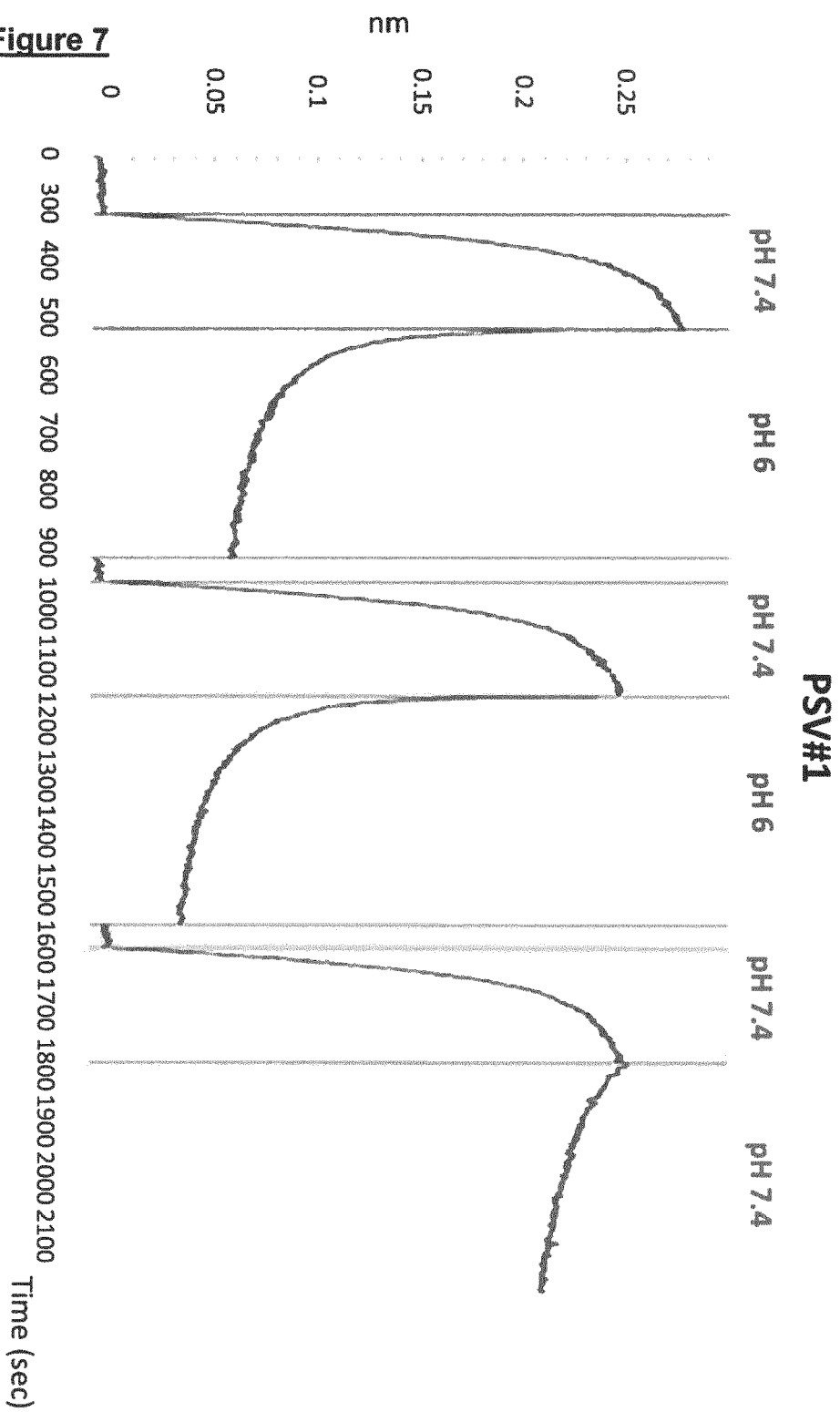
Figure 7:
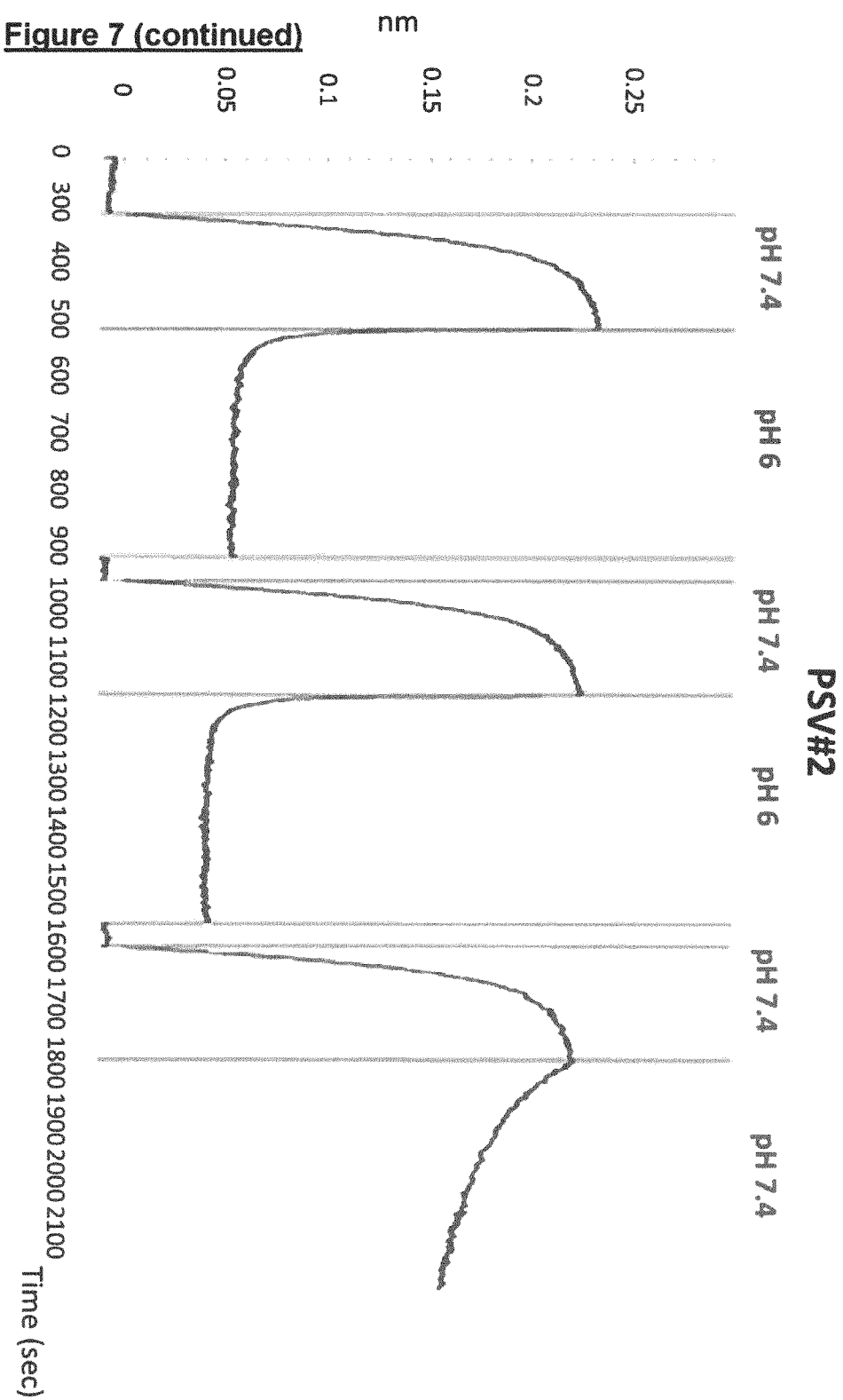
Figure 7:
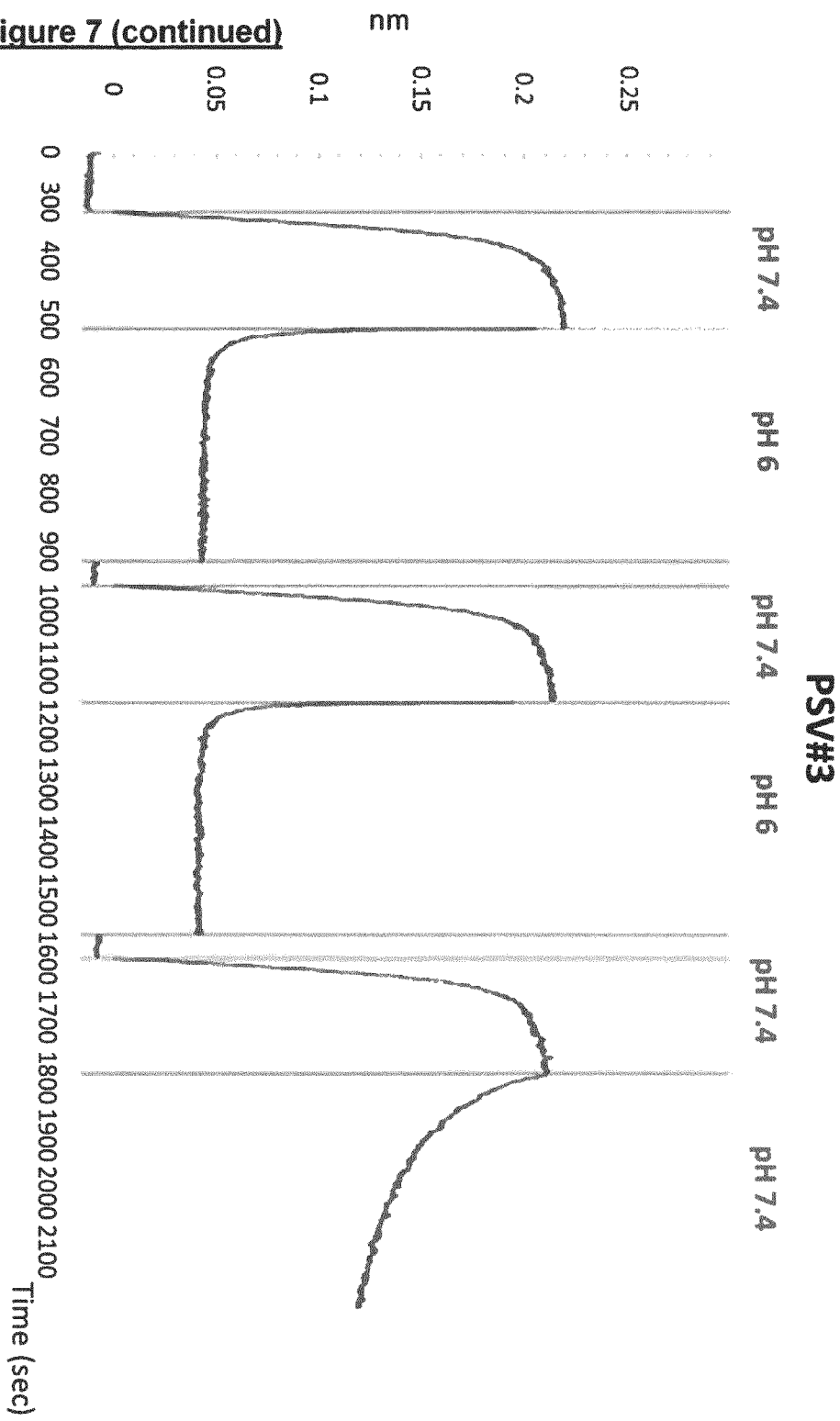
Figure 7:
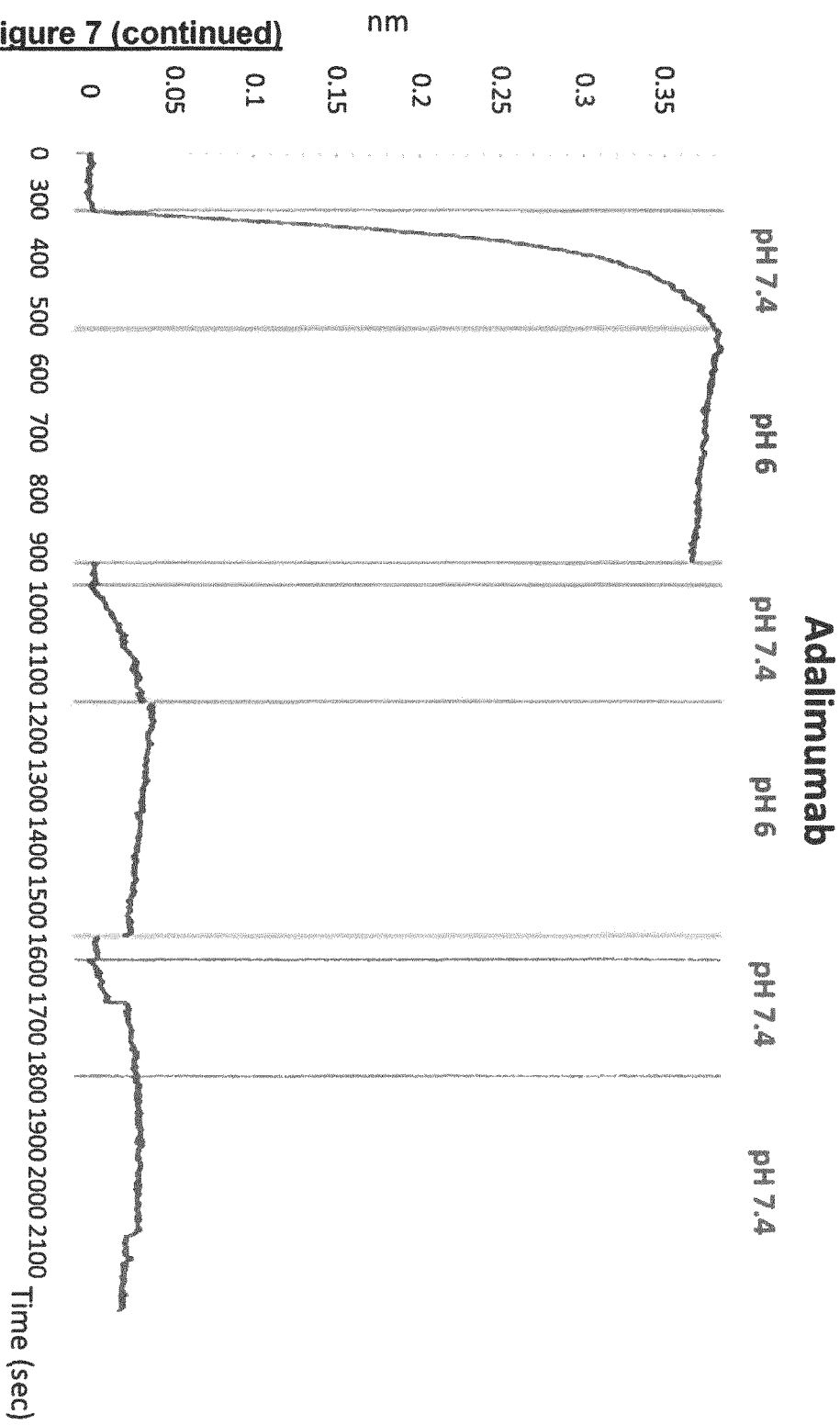

FIG. 7: Octet Red sensorgrams of adalimumab and three variants with pH-dependent binding (PSV#1, PSV#2, PSV#3). Adalimumab shows fast association of rhTNFα and maintains tight binding during the dissociation step at pH 6. In contrast, pH-dependent binding variants show reversible rhTNFα binding at pH 7.4 after fast release of rhTNFα during the dissociation step at pH 6. Association to 13 nM rhTNFα was measured for 200 sec and dissociation carried out for 400 sec. After two binding cycles the last dissociation step was done at pH 7.4, showing slow release of rhTNFα.

REFERENCES

1. Aggarwal B. B., Signalling pathways of the TNF superfamily: a double-edged sword. Nat Rev Immunol. 2003 September; 3(9):745-56. Review
2. Aggarwal R. S., What's fueling the biotech engine-2012 to 2013. Nat Biotechnol. 1 (2014) 32-9.
3. Atmanene C., Wagner-Rousset E., Malissard M., Chol B., Robert A., Corvaïa N., Van Dorsselaer A., Beck A., Sanglier-Cianférani S., Extending mass spectrometry contribution to therapeutic monoclonal antibody lead optimization: characterization of immune complexes using noncovalent ESI-MS. Anal Chem. 15 (2009) 16364-73.
4. Boder E. T., Wittrup K. D., Yeast surface display for screening combinatorial polypeptide libraries, Nat. Biotechnol. 6 (1997) 553-7
5. Carter P. J., Introduction to current and future protein therapeutics: a protein engineering perspective. Exp Cell Res. 9 (2011) 1261-9
6. Chaparro-Riggers J., Liang H., DeVay R. M., Bai L., Sutton J. E., Chen W., Geng T., Lindquist K., Casas M. G., Boustany L. M., Brown C. L., Chabot J., Gomes B., Garzone P., Rossi A., Strop P., Shelton D., Pons J., Rajpal A., Increasing serum half-life and extending cholesterol lowering in vivo by engineering antibody with pH-sensitive binding to PCSK9. J Biol Chem. 14 (2012) 11090-7.

7. Choy, E. H. S., Panayi, G. S., Cytokine pathways and joint inflammation in rheumatoid arthritis. N Engl J Med. 12 (2001) 907-16
8. Dall'Acqua W. F., Kiener P. A., Wu H., Properties of human IgG1s engineered for enhanced binding to the neonatal Fc receptor (FcRn). J Biol Chem 281 (2006) 23514-24.
9. Feldmann, M., Development of anti-TNF therapy for rheumatoid arthritis. Nat Rev Immunol 2 (2002), 364-371
10. Finkelman F. D., Madden K. B., Morris S. C., Holmes J. M., Boiani N., Katona I. M., Maliszewski C. R., Anti-cytokine antibodies as carrier proteins. Prolongation of in vivo effects of exogenous cytokines by injection of cytokine-anti-cytokine antibody complexes. J Immunol. 3 (1993) 1235-44
11. Gera N., Hill A. B., White D. P., Carbonell R. G, Rao B. M., Design of pH sensitive binding proteins from the hyperthermophilic Sso7d scaffold. PLoS One. 7 (2012)
12. Humira (adalimumab) prescribing information. Abbott Laboratories. September 2013. Available at: http://www.rxabbott.com/pdf/humira.pdf. Accessed Apr. 21, 2014.
13. Horiuchi T., Mitoma H, Harashima S, Tsukamoto H, Shimoda T. Transmembrane TNF-alpha: structure, function and interaction with anti-TNF agents. Rheumatology (Oxford). 7 (2010) 1215-28
14. Igawa T., Ishii S., Tachibana T., Maeda A., Higuchi Y., Shimaoka S., Moriyama C., Watanabe T., Takubo R., Doi Y., Wakabayashi T., Hayasaka A., Kadono S., Miyazaki T., Haraya K., Sekimori Y., Kojima T., Nabuchi Y., Aso Y., Kawabe Y., Hattori K., Antibody recycling by engineered pH-dependent antigen binding improves the duration of antigen neutralization. Nat Biotechnol. 11 (2010) 1203-7
15. Igawa T., Maeda A., Haraya K., Tachibana T., Iwayanagi Y., Mimoto F., Higuchi Y., Ishii S., Tamba S., Hironiwa N., Nagano K., Wakabayashi T., Tsunoda H., Hattori K., Engineered monoclonal antibody with novel antigen-sweeping activity in vivo. PLoS One. 8 (2013)
16. Ito W., Sakato N., Fujio H., Yutani K., Arata Y., Kurosawa Y., The His-probe method: effects of histidine residues introduced into the complementarity-determining regions of antibodies on antigen-antibody interactions at different pH values. FEBS Lett. 1 (1992) 85-8.
17. Kaymakcalan Z., Sakorafas P., Bose S., Scesney S., Xiong L., Hanzatian D. K., Salfeld J., Sasso E. H., Comparisons of affinities, avidities, and complement activation of adalimumab, infliximab, and etanercept in binding to soluble and membrane tumor necrosis factor. Clin Immunol. 2 (2009) 308-16
18. Kuo T. T., Aveson V. G., Neonatal Fc receptor and IgG-based therapeutics. MAbs. 5 (2011) 422-30
19. Murtaugh M. L., Fanning S. W., Sharma T. M., Terry A. M., Horn J. R., A combinatorial histidine scanning library approach to engineer highly pH-dependent protein switches. Protein Sci. 9 (2011) 1619-31
20. Roopenian D. C., Akilesh S., FcRn: the neonatal Fc receptor comes of age. Nat Rev Immunol. 9 (2007) 715-25
21. Sarkar C. A., Lowenhaupt K., Horan T., Boone T. C., Tidor B., Lauffenburger D. A., Rational cytokine design for increased lifetime and enhanced potency using pH-activated histidine switching. Nat Biotechnol. 9 (2002) 908-13
22. Schabert V. F., Watson C., Joseph G. J., Iversen P., Burudpakdee C., Harrison D. J., Costs of tumor necrosis factor blockers per treated patient using real-world drug data in a managed care population. J Manag Care Pharm. 8 (2013) 621-30.
23. Schottelius, A. J. G., Moldawer, L. L., Dinarello, C. A., Asadullah, K., Sterry, W., & Edwards, C. K. Biology of tumor necrosis factor-alphaimplications for psoriasis. Exp Dermatol 13 (2004) 193-222.
24. Tracey D, Klareskog L, Sasso E H, Salfeld J G, Tak P P. Tumor necrosis factor antagonist mechanisms of action: a comprehensive review. Pharmacol Ther. 2 (2008) 244-79.
25. Wajant H, Pfizenmaier K, Scheurich P. Tumor necrosis factor signaling. Cell Death Differ. 1 (2003) 45-65.

EXAMPLES

Example 1: Selection of pH-Sensitive Anti-TNFα Antibodies Derived from Adalimumab Selection of anti-TNFα antibody fragments from combinatorial histidine substitution libraries by yeast surface display: Based on the heavy and light chains of adalimumab, two antibody libraries were synthesized by Geneart, Regensburg by using pre-assembled trinucelotides building blocks. During the synthesis either parental or histidine residues were sampled whereby sampling of histidines was restricted to the complementary determining regions (CDRs) of the heavy and light chains. Most adalimumab library members carried three histidine residues that were spread over all three CDRs (FIG. 2) but variants were also synthesized that carried more or less histidine substitutions (ranging between 0 to ~20). Theoretical diversities: Heavy chain library ~10'000 variants, light chain library ~3000 variants.

Both libraries were separately subcloned into plasmid vectors by gap-repair cloning in the EBY100 yeast strain that allows covalent yeast surface display of antibody Fab-fragments (Boder and Wittrup, 1997). Corresponding parental chains were paired with the heavy or light chain libraries and the two resulting libraries were separately screened by fluorescence activated cell sorting (FACS). Cells that carried pH-sensitive adalimumab variants were subsequently enriched over three rounds of screening by applying a specific staining & selection strategy (not explained here).

Fab-fragments were selected that do reversible high affinity (KD within sub nanomolar ranges) binding to recombinant human TNFα (rhTNFα) at pH 7.4, once after rhTNFα has been released within 30 minutes at pH 6. After three rounds of screening for variants that bind to rhTNFα in pH-dependent manner, sequence analysis of isolated single clones revealed variants that carried specific histidine substitutions patterns (shown in FIGS. 3 & 4). One mutational hot-spot was identified within the CDR3 region of the heavy chain sequence data set. Two mutational hot-spots were identified within CDR-L1 and CDR-L3 regions of the light chain sequence data set. Only abundant heavy and light chain variants (occurrence within analyzed sequence set: N>1) were selected for further processing & characterization, resulting in eight light chain and three heavy chain candidates shown in Table 1 and Table 2:

TABLE 1

Three abundant (N > 1) heavy chain sequences within 38 isolated single clones after three rounds of screening.

| Abundance | Number of His substitutions (Region) | Variant code |
| --- | --- | --- |
| 29/38 | 1 (CDR H3) | VH#1 |
| 3/38 | 2 (CDR H3) | VH#2 |
| 2/38 | 2 (CDR H3) | VH#5 |

TABLE 2

Eight abundant (N > 1) light chain sequences within 98 isolated single clones after three rounds of screening.

| Abundance | Number of His substitutions (Region) | Variant code |
|---|---|---|
| 36/98 | 1 (CDR L1) | VL#3 |
| 13/98 | 2 (CDR L3) | VL#5 |
| 5/98 | 3 (CDR L3) | VL#9 |
| 4/98 | 3 (CDR L3) | VL#16 |
| 3/98 | 2 (CDR L1) | VL#14 |
| 3/98 | 1 (CDR L3) | VL#6 |
| 2/98 | 1 (CDR L1)<br>1 (CDR L3) | VL#1 |
| 2/98 | 1 (CDR L1)<br>1 (CDR L2) | VL#22 |

Variable regions of abundant VH/VL variants as well as parental adalimumab sequences were cloned into vectors that allow expression of full length IgG1 K molecules in mammalian cells (HEK293 & Expi293). All possible combinations of heavy and light chain variants were co-expressed in mammalian cells. Herein 24 heavy chain and light chain variant combinations were expressed as well as 11 IgG species that derived from combinations of the heavy or light chain variants with the corresponding parental chains. Initial Octet Red experiments with immobilized antibodies assessed differential dissociation behavior at pH 6 or pH 7.4 after associating rhTNFα at pH 7.4. Ten variants were selected according to their binding profiles in regard of high affinity binding at pH 7.4 (association/dissociation at pH 7.4) and fast release of the antigen at pH 6 (association at pH 7.4/dissociation at pH 6). For further characterization antibodies were purified via protein-A purification from crude supernatants and finally buffer was exchanged to PBS. Further octet assays revealed differences in binding at pH 7.4 and differences in rhTNFα release at pH 6.

Subsequently three variants (IDs according to FIGS. 3-4: VH#2+VL#9: PSV#1, VH#2+VL#16: PSV#2 and VH#1+VL#14: PSV#3) were selected for final characterization on Octet Red.

Binding characteristics of several histidine-mutated adalimumab variants were analyzed in Octet Red experiments. Different histidine mutations in heavy and light chains as well as different heavy and light chain variant combinations have been shown to affect binding affinities at pH 7.4 and the dissociation rates at pH 6.

A combination of several mutations including Leu98His in the heavy chain and Tyr32His, Leu33His in the light chain generated PSV#3. Light chain mutations Gln89His, Arg90His and Asn92His generated the light chain of PSV#2. The mutations Arg90His, Asn92His and Thr97His generated the light chain of PSV#1. For both, PSV#1 and PSV#2, mutations of Ser100.bHis and Ser100.cHis generated the heavy chain.

(The sequences were numbered as shown in FIGS. 3A-3B and 4A-4C according to kabat numbering. For this purpose, sequences of the variants were aligned together with the parental sequence by using Clustal Wand numbering was applied considering the rules for kabat numbering.)

Representative sensorgrams of the Octet Red measurements are shown in FIGS. 5 & 6 and corresponding mean values (N=3) of calculated kinetic parameters for adalimumab, PSV#1, PSV#2 and PSV#3 are shown in table 3.

TABLE 3

Binding kinetics of adalimumab and pH-dependent binding variants to rhTNFα at pH 7.4 and pH 6. Association rate (kon), dissociation rate (kdis) and binding affinity (KD) of adalimumab, PSV#1, PSV#2 and PSV#3 at pH 7.4. Dissociation rates were determined also at pH 6. Experiments were done at 25° C. and for every experiment mean values of triplicates are shown (exception: Adalimumab was measured at pH 6 in duplicates). Representative sensorgrams that correspond to the data are shown in FIGS. 7 and 8.

| Antibody | pH 7.4 KD (M) | pH 7.4 kon ($M^{-1}s^{-1}$) | pH 7.4 kdis ($s^{-1}$) | pH 6 kdis ($s^{-1}$) | kdis ratio pH 6/pH 7.4 | kdis ratio (pH 6) vs. adalimumab |
|---|---|---|---|---|---|---|
| Adalimumab | 0.46E−11 | 1.32E+06 | 0.55E−05 | 4.81E−05 | 9 | 1 |
| PSV#1 | 4.63E−11 | 0.67E+06 | 3.26E−05 | 754E−05 | 231 | 157 |
| PSV#2 | 7.73E−11 | 1.14E+06 | 9.35E−05 | 7340E−05 | 785 | 1527 |
| PSV#3 | 11.2E−11 | 1.93E+06 | 21.8E−05 | 11000E−05 | 505 | 2293 |

Parental adalimumab binds with high affinity to rhTNFα at pH 7.4 that was also shown in Kaymakcalan et al., 2009. For the three variants the increasing kdis-values result in a decrease in binding affinity (10-24 fold decrease in KD), however interaction with TNFα with picomolar binding affinities in the three-digit range still represents very tight binding (FIG. 5 and table 3).

Octet Red measurements were also performed to assess the antibodies' pH-sensitivities. Improved antibody efficacy in context of the FcRn-mediated recycling requires tight binding to TNFα in the circulation at pH 7.4 and its fast release in the acidic endosome. In order to evaluate the release of TNFα within the acidic endosome, dissociation was measured at pH 6 after association of rhTNFα at pH 7.4 (FIG. 6 and table 3). Ratios of dissociation rates at pH 6 and pH 7.4 were determined and all variants showed considerably increased dissociation at pH 6 (59-160 fold increased kdis at pH 6, in contrast to adalimumab with a kdis ratio (pH6/pH7.4) of 6 (table 3).

One additional experiment addressed the ability of PSV#1, PSV#2 and PSV#3 to reversibly bind rhTNFα at pH 7.4, after dissociation at pH 6. To ensure that incubation at pH 6 does not irreversibly change TNFα binding capabilities, two cycles of binding (pH 7.4) and release (pH 6) were performed (FIG. 7). As shown in FIG. 8, PSV#1, PSV#2 and PSV#3 can reversibly bind after TNFα has been released at pH 6. In contrast to that, adalimumab maintains tight binding during incubation at pH 6.

Example 2: In Vivo Characterization of Mutants

The effect of parental IgG construct and mutants thereof on the PK of human TNFα was investigated in heterozygous transgenic human FcRn mice, line 176, as well as in homozygous line 32 mice. The former line was more suitable to investigate PK differences between administered IgG constructs, while the latter mouse line provided a better FcRn protection, resulting in longer half-lives, closer to what was expected in human. This longer residence of the scavenger allowed better to evaluate the impact of the antibody on the clearance of the TNFα.

Human TNFα and scavenger were administered by SC route in predefined ratios. Plasma concentration profiles of both total scavenger and total hTNFα was investigated. pH-dependent hTNFα binding was expected to result in increased clearance of the cytokine and decreased clearance of the scavenger.

Selected tissues were collected from the mice, in order to investigate distribution of the scavenger and the target cytokine. Parental IgG were used as reference compound in this study.

The in vitro and in vivo data sets were used to establish correlations between:
- physico-chemical properties and in vivo pharmacokinetics
- FcRn affinity and in in vivo pharmacokinetics and tissue distribution The correlations were used to build a physiologically-based pharmacokinetic (PBPK) model capable of characterizing and simulating plasma and tissue pharmacokinetics.

SEQUENCE LISTING

```
<160> NUMBER OF SEQ ID NOS: 44

<210> SEQ ID NO 1
<211> LENGTH: 214
<212> TYPE: PRT
<213> ORGANISM: Artificial Sequence
<220> FEATURE:
<223> OTHER INFORMATION: Adalimumab full light chain sequence

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 2
<211> LENGTH: 107
```

```
<212> TYPE: PRT
<213> ORGANISM: Artificial Sequence
<220> FEATURE:
<223> OTHER INFORMATION: Adalimumab light chain sequence, variable
      region (VL)

<400> SEQUENCE: 2

Asp Ile Gln Met Thr Gln Ser Pro Ser Ser Leu Ser Ala Ser Val Gly
1               5                  10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys
            100                 105

<210> SEQ ID NO 3
<211> LENGTH: 11
<212> TYPE: PRT
<213> ORGANISM: Artificial Sequence
<220> FEATURE:
<223> OTHER INFORMATION: Adalimumab CDR1 sequence of VL

<400> SEQUENCE: 3

Arg Ala Ser Gln Gly Ile Arg Asn Tyr Leu Ala
1               5                  10

<210> SEQ ID NO 4
<211> LENGTH: 7
<212> TYPE: PRT
<213> ORGANISM: Artificial Sequence
<220> FEATURE:
<223> OTHER INFORMATION: Adalimumab CDR2 sequence of VL

<400> SEQUENCE: 4

Ala Ala Ser Thr Leu Gln Ser
1               5

<210> SEQ ID NO 5
<211> LENGTH: 9
<212> TYPE: PRT
<213> ORGANISM: Artificial Sequence
<220> FEATURE:
<223> OTHER INFORMATION: Adalimumab CDR3 sequence of VL

<400> SEQUENCE: 5

Gln Arg Tyr Asn Arg Ala Pro Tyr Thr
1               5

<210> SEQ ID NO 6
<211> LENGTH: 451
<212> TYPE: PRT
<213> ORGANISM: Artificial Sequence
<220> FEATURE:
<223> OTHER INFORMATION: Adalimumab full heavy chain sequence

<400> SEQUENCE: 6

Glu Val Gln Leu Val Glu Ser Gly Gly Gly Leu Val Gln Pro Gly Arg
```

-continued

```
1               5                   10                  15
Ser Leu Arg Leu Ser Cys Ala Ala Ser Gly Phe Thr Phe Asp Asp Tyr
            20                  25                  30
Ala Met His Trp Val Arg Gln Ala Pro Gly Lys Gly Leu Glu Trp Val
            35                  40                  45
Ser Ala Ile Thr Trp Asn Ser Gly His Ile Asp Tyr Ala Asp Ser Val
50                  55                  60
Glu Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Val Tyr Tyr Cys
                85                  90                  95
Ala Lys Val Ser Tyr Leu Ser Thr Ala Ser Ser Leu Asp Tyr Trp Gly
                100                 105                 110
Gln Gly Thr Leu Val Thr Val Ser Ser Ala Ser Thr Lys Gly Pro Ser
                115                 120                 125
Val Phe Pro Leu Ala Pro Ser Ser Lys Ser Thr Ser Gly Gly Thr Ala
                130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
                180                 185                 190
Pro Ser Ser Ser Leu Gly Thr Gln Thr Tyr Ile Cys Asn Val Asn His
                195                 200                 205
Lys Pro Ser Asn Thr Lys Val Asp Lys Lys Val Glu Pro Lys Ser Cys
    210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
                260                 265                 270
Glu Asp Pro Glu Val Lys Phe Asn Trp Tyr Val Asp Gly Val Glu Val
            275                 280                 285
His Asn Ala Lys Thr Lys Pro Arg Glu Glu Gln Tyr Asn Ser Thr Tyr
            290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
                340                 345                 350
Tyr Thr Leu Pro Pro Ser Arg Asp Glu Leu Thr Lys Asn Gln Val Ser
                355                 360                 365
Leu Thr Cys Leu Val Lys Gly Phe Tyr Pro Ser Asp Ile Ala Val Glu
        370                 375                 380
Trp Glu Ser Asn Gly Gln Pro Glu Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
                420                 425                 430
```

His Glu Ala Leu His Asn His Tyr Thr Gln Lys Ser Leu Ser Leu Ser
            435                 440                 445
Pro Gly Lys
    450

<210> SEQ ID NO 7
<211> LENGTH: 121
<212> TYPE: PRT
<213> ORGANISM: Artificial Sequence
<220> FEATURE:
<223> OTHER INFORMATION: Adalimumab heavy chain sequence, variable
      region (VH)

<400> SEQUENCE: 7

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser
        115                 120

<210> SEQ ID NO 8
<211> LENGTH: 5
<212> TYPE: PRT
<213> ORGANISM: Artificial Sequence
<220> FEATURE:
<223> OTHER INFORMATION: Adalimumab CDR1 sequence of VH

<400> SEQUENCE: 8

Asp Tyr Ala Met His
1               5

<210> SEQ ID NO 9
<211> LENGTH: 17
<212> TYPE: PRT
<213> ORGANISM: Artificial Sequence
<220> FEATURE:
<223> OTHER INFORMATION: Adalimumab CDR2 sequence of VH

<400> SEQUENCE: 9

Ala Ile Thr Trp Asn Ser Gly His Ile Asp Tyr Ala Asp Ser Val Glu
1               5                   10                  15

Gly

<210> SEQ ID NO 10
<211> LENGTH: 12
<212> TYPE: PRT
<213> ORGANISM: Artificial Sequence
<220> FEATURE:
<223> OTHER INFORMATION: Adalimumab CDR3 sequence of VH

<400> SEQUENCE: 10

Val Ser Tyr Leu Ser Thr Ala Ser Ser Leu Asp Tyr
1               5                   10

<210> SEQ ID NO 11
<211> LENGTH: 330
<212> TYPE: PRT
<213> ORGANISM: Artificial Sequence
<220> FEATURE:
<223> OTHER INFORMATION: Adalimumab human heavy chain IgG1 constant
      region

<400> SEQUENCE: 11

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

-continued

```
<210> SEQ ID NO 12
<211> LENGTH: 12
<212> TYPE: PRT
<213> ORGANISM: Artificial Sequence
<220> FEATURE:
<223> OTHER INFORMATION: adalimumab mutated CDR3 heavy chain

<400> SEQUENCE: 12

Val Ser Tyr His Ser Thr Ala Ser Ser Leu Asp Tyr
1               5                   10

<210> SEQ ID NO 13
<211> LENGTH: 12
<212> TYPE: PRT
<213> ORGANISM: Artificial Sequence
<220> FEATURE:
<223> OTHER INFORMATION: Adalimumab mutated CDR3 heavy chain

<400> SEQUENCE: 13

Val Ser Tyr Leu Ser Thr Ala His His Leu Asp Tyr
1               5                   10

<210> SEQ ID NO 14
<211> LENGTH: 12
<212> TYPE: PRT
<213> ORGANISM: Artificial Sequence
<220> FEATURE:
<223> OTHER INFORMATION: Adalimumab mutated  CDR3 heavy chain

<400> SEQUENCE: 14

Val Ser Tyr His Ser Thr Ala His His Leu Asp Tyr
1               5                   10

<210> SEQ ID NO 15
<211> LENGTH: 11
<212> TYPE: PRT
<213> ORGANISM: Artificial Sequence
<220> FEATURE:
<223> OTHER INFORMATION: Adalimumab mutated  CDR1 light chain

<400> SEQUENCE: 15

Arg Ala Ser Gln Gly Ile Arg Asn His Leu Ala
1               5                   10

<210> SEQ ID NO 16
<211> LENGTH: 11
<212> TYPE: PRT
<213> ORGANISM: Artificial Sequence
<220> FEATURE:
<223> OTHER INFORMATION: Adalimumab mutated  CDR1 light chain

<400> SEQUENCE: 16

Arg Ala Ser Gln Gly Ile Arg Asn His His Ala
1               5                   10

<210> SEQ ID NO 17
<211> LENGTH: 9
<212> TYPE: PRT
<213> ORGANISM: Artificial Sequence
<220> FEATURE:
<223> OTHER INFORMATION: Adalimumab mutated CDR3 light chain

<400> SEQUENCE: 17

His His Tyr His Arg Ala Pro Tyr Thr
1               5

<210> SEQ ID NO 18
```

```
<211> LENGTH: 9
<212> TYPE: PRT
<213> ORGANISM: Artificial Sequence
<220> FEATURE:
<223> OTHER INFORMATION: Adalimumab mutated CDR3 light chain

<400> SEQUENCE: 18

Gln His Tyr His Arg Ala Pro Tyr His
1               5

<210> SEQ ID NO 19
<211> LENGTH: 9
<212> TYPE: PRT
<213> ORGANISM: Artificial Sequence
<220> FEATURE:
<223> OTHER INFORMATION: Adalimumab mutated a CDR3 light chain, wherein
      X1 is Q or H and X2 is T or H
<220> FEATURE:
<221> NAME/KEY: X1
<222> LOCATION: (1)..(1)
<223> OTHER INFORMATION: x1 is Q or H
<220> FEATURE:
<221> NAME/KEY: X2
<222> LOCATION: (9)..(9)
<223> OTHER INFORMATION: x2 is T or H

<400> SEQUENCE: 19

Xaa His Tyr His Arg Ala Pro Tyr Xaa
1               5

<210> SEQ ID NO 20
<211> LENGTH: 107
<212> TYPE: PRT
<213> ORGANISM: Artificial Sequence
<220> FEATURE:
<223> OTHER INFORMATION: histidine-mutated adalimumab light chain
      variable region, wherein X1 is L or H
<220> FEATURE:
<221> NAME/KEY: x
<222> LOCATION: (33)..(33)
<223> OTHER INFORMATION: X is L or H
<220> FEATURE:
<221> NAME/KEY: X1
<222> LOCATION: (33)..(33)
<223> OTHER INFORMATION: X1 is L or H

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn His
            20                  25                  30

Xaa Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys
            100                 105

<210> SEQ ID NO 21
<211> LENGTH: 107
<212> TYPE: PRT
<213> ORGANISM: Artificial Sequence
<220> FEATURE:
```

```
<223> OTHER INFORMATION: histidine-mutated adalimumab light chain
      variable region, wherein X1 is Q or H   and X2 is T or H
<220> FEATURE:
<221> NAME/KEY: X1
<222> LOCATION: (89)..(89)
<223> OTHER INFORMATION: X1 is Q or H
<220> FEATURE:
<221> NAME/KEY: X2
<222> LOCATION: (97)..(97)
<223> OTHER INFORMATION: X2 is T or H

<400> SEQUENCE: 21

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Xaa His Tyr His Arg Ala Pro Tyr
                85                  90                  95

Xaa Phe Gly Gln Gly Thr Lys Val Glu Ile Lys
            100                 105

<210> SEQ ID NO 22
<211> LENGTH: 107
<212> TYPE: PRT
<213> ORGANISM: Artificial Sequence
<220> FEATURE:
<223> OTHER INFORMATION: histidine-mutated adalimumab light chain
      variable region, wherein X1 is T or H
<220> FEATURE:
<221> NAME/KEY: X1
<222> LOCATION: (97)..(97)
<223> OTHER INFORMATION: X1 is T or H

<400> SEQUENCE: 22

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys His His Tyr His Arg Ala Pro Tyr
                85                  90                  95

Xaa Phe Gly Gln Gly Thr Lys Val Glu Ile Lys
            100                 105

<210> SEQ ID NO 23
<211> LENGTH: 107
<212> TYPE: PRT
<213> ORGANISM: Artificial Sequence
<220> FEATURE:
<223> OTHER INFORMATION: histidine-mutated adalimumab light chain
      variable region, wherein X1 is Q or H
<220> FEATURE:
```

```
<221> NAME/KEY: X1
<222> LOCATION: (89)..(89)
<223> OTHER INFORMATION: X1 is Q or H

<400> SEQUENCE: 23

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Xaa His Tyr His Arg Ala Pro Tyr
                85                  90                  95

His Phe Gly Gln Gly Thr Lys Val Glu Ile Lys
            100                 105

<210> SEQ ID NO 24
<211> LENGTH: 107
<212> TYPE: PRT
<213> ORGANISM: Artificial Sequence
<220> FEATURE:
<223> OTHER INFORMATION: histidine-mutated adalimumab light chain
      variable region, ), wherein X1 is L or H,  and  X2 is Q or H and
      X3 is T or H
<220> FEATURE:
<221> NAME/KEY: X1
<222> LOCATION: (33)..(33)
<223> OTHER INFORMATION: X1 is L or H
<220> FEATURE:
<221> NAME/KEY: X2
<222> LOCATION: (89)..(89)
<223> OTHER INFORMATION: X2 is Q or H
<220> FEATURE:
<221> NAME/KEY: X3
<222> LOCATION: (97)..(97)
<223> OTHER INFORMATION: X3 is T or H

<400> SEQUENCE: 24

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn His
            20                  25                  30

Xaa Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Xaa His Tyr His Arg Ala Pro Tyr
                85                  90                  95

Xaa Phe Gly Gln Gly Thr Lys Val Glu Ile Lys
            100                 105

<210> SEQ ID NO 25
<211> LENGTH: 121
<212> TYPE: PRT
<213> ORGANISM: Artificial Sequence
<220> FEATURE:
<223> OTHER INFORMATION: histidine-mutated adalimumab heavy chain
``` variable region

<400> SEQUENCE: 25

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr His Ser Thr Ala Ser Ser Leu Asp Tyr Trp Gly
            100                 105                 110

Gln Gly Thr Leu Val Thr Val Ser Ser
        115                 120

<210> SEQ ID NO 26
<211> LENGTH: 121
<212> TYPE: PRT
<213> ORGANISM: Artificial Sequence
<220> FEATURE:
<223> OTHER INFORMATION: histidine-mutated adalimumab comprising the
      variable heavy chain sequence

<400> SEQUENCE: 26

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala His His Leu Asp Tyr Trp Gly
            100                 105                 110

Gln Gly Thr Leu Val Thr Val Ser Ser
        115                 120

<210> SEQ ID NO 27
<211> LENGTH: 107
<212> TYPE: PRT
<213> ORGANISM: Artificial Sequence
<220> FEATURE:
<223> OTHER INFORMATION: histidine-mutated adalimumab comprising the
      variable heavy chain sequence

<400> SEQUENCE: 27

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn His
            20                  25                  30

His Ala Trp Tyr Gln Gln Lys Pro Gly Lys Ala Pro Lys Leu Leu Ile
            35                  40                  45

Tyr Ala Ala Ser Thr Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys
            100                 105

<210> SEQ ID NO 28
<211> LENGTH: 107
<212> TYPE: PRT
<213> ORGANISM: Artificial Sequence
<220> FEATURE:
<223> OTHER INFORMATION: histidine-mutated adalimumab variable light
      chain sequence

<400> SEQUENCE: 28

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
            35                  40                  45

Tyr Ala Ala Ser Thr Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys His His Tyr His Arg Ala Pro Tyr
                85                  90                  95

Thr Phe Gly Gln Gly Thr Lys Val Glu Ile Lys
            100                 105

<210> SEQ ID NO 29
<211> LENGTH: 107
<212> TYPE: PRT
<213> ORGANISM: Artificial Sequence
<220> FEATURE:
<223> OTHER INFORMATION: histidine-mutated adalimumab variable light
      chain

<400> SEQUENCE: 29

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
            35                  40                  45

Tyr Ala Ala Ser Thr Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln His Tyr His Arg Ala Pro Tyr
                85                  90                  95

His Phe Gly Gln Gly Thr Lys Val Glu Ile Lys
            100                 105

<210> SEQ ID NO 30
<211> LENGTH: 107
<212> TYPE: PRT
<213> ORGANISM: Artificial Sequence
<220> FEATURE:
<223> OTHER INFORMATION: histidine-mutated adalimumab variable light
      chain

<400> SEQUENCE: 30

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln His Tyr His Arg Ala Pro Tyr
                85                  90                  95

His Phe Gly Gln Gly Thr Lys Val Glu Ile Lys
            100                 105

<210> SEQ ID NO 31
<211> LENGTH: 12
<212> TYPE: PRT
<213> ORGANISM: Artificial Sequence
<220> FEATURE:
<223> OTHER INFORMATION: mutated adalimumab CDR3 heavy chain

<400> SEQUENCE: 31

Val His Tyr His Ser Thr Ala Ser Ser Leu Asp Tyr
1               5                   10

<210> SEQ ID NO 32
<211> LENGTH: 7
<212> TYPE: PRT
<213> ORGANISM: Artificial Sequence
<220> FEATURE:
<223> OTHER INFORMATION: mutated adalimumab CDR2 light chain

<400> SEQUENCE: 32

Ala Ala His Thr Leu Gln Ser
1               5

<210> SEQ ID NO 33
<211> LENGTH: 107
<212> TYPE: PRT
<213> ORGANISM: Artificial Sequence
<220> FEATURE:
<223> OTHER INFORMATION: histidine-mutated adalimumab light chain
      variable region

<400> SEQUENCE: 33

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
            50                  55                  60

Ser Gly Ser Gly Thr Asp Phe Thr Leu Thr Ile Ser Ser Leu Gln Pro
 65                  70                  75                  80

Glu Asp Val Ala Thr Tyr Tyr Cys Gln His Tyr His Arg Ala Pro Tyr
                85                  90                  95

Thr Phe Gly Gln Gly Thr Lys Val Glu Ile Lys
            100                 105

<210> SEQ ID NO 34
<211> LENGTH: 107
<212> TYPE: PRT
<213> ORGANISM: Artificial Sequence
<220> FEATURE:
<223> OTHER INFORMATION: histidine-mutated adalimumab light chain
      variable region

<400> SEQUENCE: 34

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn His
                20                  25                  30

Leu Ala Trp Tyr Gln Gln Lys Pro Gly Lys Ala Pro Lys Leu Leu Ile
            35                  40                  45

Tyr Ala Ala Ser Thr Leu Gln Ser Gly Val Pro Ser Arg Phe Ser Gly
            50                  55                  60

Ser Gly Ser Gly Thr Asp Phe Thr Leu Thr Ile Ser Ser Leu Gln Pro
 65                  70                  75                  80

Glu Asp Val Ala Thr Tyr Tyr Cys Gln Arg Tyr Asn His Ala Pro Tyr
                85                  90                  95

Thr Phe Gly Gln Gly Thr Lys Val Glu Ile Lys
            100                 105

<210> SEQ ID NO 35
<211> LENGTH: 107
<212> TYPE: PRT
<213> ORGANISM: Artificial Sequence
<220> FEATURE:
<223> OTHER INFORMATION: histidine-mutated adalimumab light chain
      variable region

<400> SEQUENCE: 35

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn His
                20                  25                  30

Leu Ala Trp Tyr Gln Gln Lys Pro Gly Lys Ala Pro Lys Leu Leu Ile
            35                  40                  45

Tyr Ala Ala Ser Thr Leu Gln Ser Gly Val Pro Ser Arg Phe Ser Gly
            50                  55                  60

Ser Gly Ser Gly Thr Asp Phe Thr Leu Thr Ile Ser Ser Leu Gln Pro
 65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys
            100                 105

<210> SEQ ID NO 36
<211> LENGTH: 107

```
<212> TYPE: PRT
<213> ORGANISM: Artificial Sequence
<220> FEATURE:
<223> OTHER INFORMATION: histidine-mutated adalimumab light chain
      variable region

<400> SEQUENCE: 36

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg His Asn Arg Ala Pro Tyr
                85                  90                  95

Thr Phe Gly Gln Gly Thr Lys Val Glu Ile Lys
            100                 105

<210> SEQ ID NO 37
<211> LENGTH: 107
<212> TYPE: PRT
<213> ORGANISM: Artificial Sequence
<220> FEATURE:
<223> OTHER INFORMATION: histidine-mutated adalimumab light chain
      variable region

<400> SEQUENCE: 37

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn His
            20                  25                  30

Leu Ala Trp Tyr Gln Gln Lys Pro Gly Lys Ala Pro Lys Leu Leu Ile
        35                  40                  45

Tyr Ala Ala His Thr Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys
            100                 105

<210> SEQ ID NO 38
<211> LENGTH: 9
<212> TYPE: PRT
<213> ORGANISM: Artificial Sequence
<220> FEATURE:
<223> OTHER INFORMATION: mutated adalimumab CDR3 light chain

<400> SEQUENCE: 38

Gln Arg His Asn Arg Ala Pro Tyr Thr
1               5

<210> SEQ ID NO 39
<211> LENGTH: 121
<212> TYPE: PRT
<213> ORGANISM: Artificial Sequence
```

<220> FEATURE:
<223> OTHER INFORMATION: mutated adalimumab variable heavy chain

<400> SEQUENCE: 39

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val His Tyr His Ser Thr Ala Ser Ser Leu Asp Tyr Trp Gly
            100                 105                 110

Gln Gly Thr Leu Val Thr Val Ser Ser
        115                 120

<210> SEQ ID NO 40
<211> LENGTH: 12
<212> TYPE: PRT
<213> ORGANISM: Artificial Sequence
<220> FEATURE:
<223> OTHER INFORMATION: mutated adalimumab CDR3 heavy chain, wherein
      X1 is S or H; X2 is L or H, X3 = S or H, and X4 is S or H, and
      wherein at least X1 or X2 or X3 or X4 is H
<220> FEATURE:
<221> NAME/KEY: X1
<222> LOCATION: (2)..(2)
<223> OTHER INFORMATION: X1 is S or H
<220> FEATURE:
<221> NAME/KEY: X2
<222> LOCATION: (4)..(4)
<223> OTHER INFORMATION: X2 is L or H
<220> FEATURE:
<221> NAME/KEY: X3
<222> LOCATION: (8)..(8)
<223> OTHER INFORMATION: X3 is S or H
<220> FEATURE:
<221> NAME/KEY: X4
<222> LOCATION: (9)..(9)
<223> OTHER INFORMATION: X4 is S or H

<400> SEQUENCE: 40

Val Xaa Tyr Xaa Ser Thr Ala Xaa Xaa Leu Asp Tyr
1               5                   10

<210> SEQ ID NO 41
<211> LENGTH: 9
<212> TYPE: PRT
<213> ORGANISM: Artificial Sequence
<220> FEATURE:
<223> OTHER INFORMATION: mutated adalimumab CDR3 light chain, wherein X1
      is Q or H, X2 is R or H, X3 is Y or H, X4 is N or H, and X5 is T
      or H, wherein at least  X1 or X2 or X3 or X4 or X5 is H
<220> FEATURE:
<221> NAME/KEY: X1
<222> LOCATION: (1)..(1)
<223> OTHER INFORMATION: X1 is Q or H
<220> FEATURE:
<221> NAME/KEY: X2
<222> LOCATION: (2)..(2)
<223> OTHER INFORMATION: X2 is R or H
<220> FEATURE:
<221> NAME/KEY: X3

```
<222> LOCATION: (3)..(3)
<223> OTHER INFORMATION: X3 is Y or H
<220> FEATURE:
<221> NAME/KEY: X4
<222> LOCATION: (4)..(4)
<223> OTHER INFORMATION: X4 is N or H
<220> FEATURE:
<221> NAME/KEY: X5
<222> LOCATION: (9)..(9)
<223> OTHER INFORMATION: X5 is T or H

<400> SEQUENCE: 41

Xaa Xaa Xaa Xaa Arg Ala Pro Tyr Xaa
1               5

<210> SEQ ID NO 42
<211> LENGTH: 11
<212> TYPE: PRT
<213> ORGANISM: Artificial Sequence
<220> FEATURE:
<223> OTHER INFORMATION: mutated adalimumab CDR1 light chain, wherein
      X1 is Y or H, X2 is L or H, wherein at least X1 or X2 is H.
<220> FEATURE:
<221> NAME/KEY: X1
<222> LOCATION: (9)..(9)
<223> OTHER INFORMATION: X1 is Y or H
<220> FEATURE:
<221> NAME/KEY: X2
<222> LOCATION: (10)..(10)
<223> OTHER INFORMATION: X2 is L or H

<400> SEQUENCE: 42

Arg Ala Ser Gln Gly Ile Arg Asn Xaa Xaa Ala
1               5                   10

<210> SEQ ID NO 43
<211> LENGTH: 107
<212> TYPE: PRT
<213> ORGANISM: Artificial Sequence
<220> FEATURE:
<223> OTHER INFORMATION: mutated adalimumab light chain variable region,
      wherein X1 is Y or H, X2 is L or H, X3 is S or H, X4 is Q or H, X5
      is R or H, X6 is Y or H, X7 is N or H, X8 is T or H, wherein at
      least X1 or X2 or X3 or X4 or X5 or X6 or X7 or X8 is H.
<220> FEATURE:
<221> NAME/KEY: X1
<222> LOCATION: (32)..(32)
<223> OTHER INFORMATION: X1 is Y or H
<220> FEATURE:
<221> NAME/KEY: X8
<222> LOCATION: (33)..(33)
<223> OTHER INFORMATION: X8 is L or H
<220> FEATURE:
<221> NAME/KEY: X7
<222> LOCATION: (52)..(52)
<223> OTHER INFORMATION: X7 is S or H
<220> FEATURE:
<221> NAME/KEY: X2
<222> LOCATION: (89)..(89)
<223> OTHER INFORMATION: X2 is Q or H
<220> FEATURE:
<221> NAME/KEY: X3
<222> LOCATION: (90)..(90)
<223> OTHER INFORMATION: X3 is R or H
<220> FEATURE:
<221> NAME/KEY: X4
<222> LOCATION: (91)..(91)
<223> OTHER INFORMATION: X4 is Y or H
<220> FEATURE:
<221> NAME/KEY: X5
<222> LOCATION: (92)..(92)
<223> OTHER INFORMATION: X5 is N or H
<220> FEATURE:
<221> NAME/KEY: X6
<222> LOCATION: (97)..(97)
```

<223> OTHER INFORMATION: X6 is T or H

<400> SEQUENCE: 43

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Xaa
            20                  25                  30

Xaa Ala Trp Tyr Gln Gln Lys Pro Gly Lys Ala Pro Lys Leu Leu Ile
        35                  40                  45

Tyr Ala Ala Xaa Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Xaa Xaa Xaa Xaa Arg Ala Pro Tyr
                85                  90                  95

Xaa Phe Gly Gln Gly Thr Lys Val Glu Ile Lys
            100                 105

<210> SEQ ID NO 44
<211> LENGTH: 121
<212> TYPE: PRT
<213> ORGANISM: Artificial Sequence
<220> FEATURE:
<223> OTHER INFORMATION: mutated adalimumab heavy chain variable region,
      wherein X1 is S or H, X2 is L or H, X3 is S or H, X4 is S or H,
      wherein at least X1 or X2 or X3 or X4 is H.
<220> FEATURE:
<221> NAME/KEY: X1
<222> LOCATION: (100)..(100)
<223> OTHER INFORMATION: X1 is S or H
<220> FEATURE:
<221> NAME/KEY: X2
<222> LOCATION: (102)..(102)
<223> OTHER INFORMATION: X2 is L or H
<220> FEATURE:
<221> NAME/KEY: X3
<222> LOCATION: (106)..(106)
<223> OTHER INFORMATION: X3 is S or H
<220> FEATURE:
<221> NAME/KEY: X4
<222> LOCATION: (107)..(107)
<223> OTHER INFORMATION: X4 is S or H

<400> SEQUENCE: 44

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Xaa Tyr Xaa Ser Thr Ala Xaa Xaa Leu Asp Tyr Trp Gly
            100                 105                 110

Gln Gly Thr Leu Val Thr Val Ser Ser
            115                 120

The invention claimed is:

1. A human antibody or an antigen binding fragment thereof with a pH dependent antigen binding, comprising: light and heavy chain variable regions of human antibody adalimumab or a variant thereof with the same or similar TNF-binding activity, wherein at least one of the CDR domains of the light chain variable region is mutated by replacement of from one to four amino acids within said CDR domains by a histidine residue and/or the CDR-H3 domain of the heavy chain variable region is mutated by replacement of one or two amino acids within said CDR domains by a histidine residue, thereby generating a mutated adalimumab or adalimumab variant eliciting a pH dependent antigen binding with an antigen dissociation rate ($K_{dis}$) ratio pH 6/pH 7 measured by biolayer interferometry which is at least 5 fold higher compared to a respective $K_{dis}$ rate ratio of non-mutated adalimumab.

2. The human antibody or the antigen binding fragment thereof of claim 1, wherein the mutated antibody or antigen binding fragment thereof has a reduced antigen binding affinity, which is at least 1% of the binding affinity of the non-mutated adalimumab.

3. The human antibody or the antigen binding fragment thereof of claim 1, comprising a CDR3 heavy chain amino acid sequence selected from the group consisting of:

```
                            (SEQ ID NO: 12)
VSYHSTASSLDY, (SEQ ID NO: 13)
VSYLSTAHHLDY, (SEQ ID NO: 14)
VSYHSTAHHLDY,
and (SEQ ID NO: 31)
VHYHSTASSLDY.
```

4. The human antibody or the antigen binding fragment thereof of claim 1, comprising a CDR1 light chain amino acid sequence selected from the group consisting of:

```
                            (SEQ ID NO: 15)
RASQGIRNHLA
and (SEQ ID NO: 16)
RASQGIRNHHA.
```

5. The human antibody or the antigen binding fragment thereof of claim 1, comprising the CDR2 light chain amino acid sequence of:

```
                            (SEQ ID NO: 32)
AAHTLQS.
```

6. The human antibody or the antigen binding fragment thereof of claim 1, comprising a CDR3 light chain amino acid sequence selected from the group consisting of:

```
                            (SEQ ID NO: 17)
HHYHRAPYT, (SEQ ID NO: 18)
QHYHRAPYH
and (SEQ ID NO: 38)
QRHNRAPYT.
```

7. The human antibody or the antigen binding fragment thereof of claim 1, comprising:

a CDR3 heavy chain amino acid sequence selected from the group consisting of

```
                            (SEQ ID NO: 12)
VSYHSTASSLDY, (SEQ ID NO: 13)
VSYLSTAHHLDY, (SEQ ID NO: 14)
VSYHSTAHHLDY,
and (SEQ ID NO: 31)
VHYHSTASSLDY,
and
``` a CDR1 light chain amino acid sequence selected from the group consisting of

```
                            (SEQ ID NO: 15)
RASQGIRNHLA
and (SEQ ID NO: 16)
RASQGIRNHHA.
```

8. The human antibody or the antigen binding fragment thereof of claim 1, comprising:

a CDR3 heavy chain amino acid sequence selected from the group consisting of

```
                            (SEQ ID NO: 12)
VSYHSTASSLDY, (SEQ ID NO: 13)
VSYLSTAHHLDY, (SEQ ID NO: 14)
VSYHSTAHHLDY,
and (SEQ ID NO: 31)
VHYHSTASSLDY,
and
``` a CDR3 light chain amino acid sequence selected from the group consisting of

```
                            (SEQ ID NO: 17)
HHYHRAPYT, (SEQ ID NO: 18)
QHYHRAPYH,
and (SEQ ID NO: 38)
QRHNRAPYT.
```

9. The human antibody or the antigen binding fragment thereof of claim 1, comprising:

a CDR3 heavy chain amino acid sequence selected from the group consisting of

VSYHSTASSLDY,                    (SEQ ID NO: 12)

VSYLSTAHHLDY,                    (SEQ ID NO: 13)

VSYHSTAHHLDY,                    (SEQ ID NO: 14)
and

VHYHSTASSLDY,                    (SEQ ID NO: 31)

the CDR2 light chain amino acid sequence AAHTLQS (SEQ ID NO: 32), and
a CDR3 light chain amino acid sequence selected from the group consisting of

HHYHRAPYT,                       (SEQ ID NO: 17)

QHYHRAPYH,                       (SEQ ID NO: 18)
and

QRHNRAPYT.                       (SEQ ID NO: 38)

10. The human antibody or the antigen binding fragment thereof of claim 1, comprising:
a CDR3 heavy chain amino acid sequence selected from the group consisting of

VSYHSTASSLDY,                    (SEQ ID NO: 12)

VSYLSTAHHLDY,                    (SEQ ID NO: 13)

VSYHSTAHHLDY,                    (SEQ ID NO: 14)
and

VHYHSTASSLDY,                    (SEQ ID NO: 31)

a CDR1 light chain amino acid sequence selected from the group consisting of

RASQGIRNHLA                      (SEQ ID NO: 15)
and

RASQGIRNHHA,                     (SEQ ID NO: 16)

a CDR3 light chain amino acid sequence selected from the group consisting of

HHYHRAPYT,                       (SEQ ID NO: 17)

QHYHRAPYH,                       (SEQ ID NO: 18)
and

QRHNRAPYT.                       (SEQ ID NO: 38)

11. The human antibody or the antigen binding fragment thereof of claim 1, comprising a variable light chain amino acid sequence selected from the group consisting of (i)
                                 (SEQ ID NO: 28)
DIQMTQSPSS LSASVGDRVT ITCRASQGIR NHHAWYQQKP
GKAPKLLIYA ASTLQSGVPS RFSGSGSGTD FTLTISSLQP
EDVATYYCQR YNRAPYTFGQ GTKVEIK, (ii)
                                 (SEQ ID NO: 29)
DIQMTQSPSS LSASVGDRVT ITCRASQGIR NYLAWYQQKP
GKAPKLLIYA ASTLQSGVPS RFSGSGSGTD FTLTISSLQP
EDVATYYCHH YHRAPYTFGQ GTKVEIK, (iii)
                                 (SEQ ID NO: 30)
DIQMTQSPSS LSASVGDRVT ITCRASQGIR NYLAWYQQKP
GKAPKLLIYA ASTLQSGVPS RFSGSGSGTD FTLTISSLQP
EDVATYYCQH YHRAPYHFGQ GTKVEIK, (iv)
                                 (SEQ ID NO: 33)
DIQMTQSPSS LSASVGDRVT ITCRASQGIR NYLAWYQQKP
GKAPKLLIYA ASTLQSGVPS RFSGSGSGTD FTLTISSLQP
EDVATYYCQH YHRAPYTFGQ GTKVEIK, (v)
                                 (SEQ ID NO: 34)
DIQMTQSPSS LSASVGDRVT ITCRASQGIR NHLAWYQQKP
GKAPKLLIYA ASTLQSGVPS RFSGSGSGTD FTLTISSLQP
EDVATYYCQR YNHAPYTFGQ GTKVEIK, (vi)
                                 (SEQ ID NO: 35)
DIQMTQSPSS LSASVGDRVT ITCRASQGIR NHLAWYQQKP
GKAPKLLIYA ASTLQSGVPS RFSGSGSGTD FTLTISSLQP
EDVATYYCQR YNRAPYTFGQ GTKVEIK, (vii)
                                 (SEQ ID NO: 36)
DIQMTQSPSS LSASVGDRVT ITCRASQGIR NYLAWYQQKP
GKAPKLLIYA ASTLQSGVPS RFSGSGSGTD FTLTISSLQP
EDVATYYCQR HNRAPYTFGQ GTKVEIK,
and (viii)
                                 (SEQ ID NO: 37)
DIQMTQSPSS LSASVGDRVT ITCRASQGIR NHLAWYQQKP
GKAPKLLIYA AHTLQSGVPS RFSGSGSGTD FTLTISSLQP
EDVATYYCQR YNRAPYTFGQ GTKVEIK.

12. The human antibody or the antigen binding fragment thereof of claim 1, comprising a variable heavy chain amino acid sequence selected from the group consisting of:

(i)
                                 (SEQ ID NO: 25)
EVQLVESGGG LVQPGRSLRL SCAASGFTFD DYAMHWVRQA
PGKGLEWVSA ITWNSGHIDY ADSVEGRFTI SRDNAKNSLY
LQMNSLRAED TAVYYCAKVS YHSTASSLDY WGQGTLVTVS S;

(ii)
                                 (SEQ ID NO: 26)
EVQLVESGGG LVQPGRSLRL SCAASGFTFD DYAMHWVRQA
PGKGLEWVSA ITWNSGHIDY ADSVEGRFTI SRDNAKNSLY
LQMNSLRAED TAVYYCAKVS YLSTAHHLDY WGQGTLVTVS S;
and (iii)
                                 (SEQ ID NO: 39)
EVQLVESGGG LVQPGRSLRL SCAASGFTFD DYAMHWVRQA
PGKGLEWVSA ITWNSGHIDY ADSVEGRFTI SRDNAKNSLY
LQMNSLRAED TAVYYCAKVH YHSTASSLDY WGQGTLVTVS S.

13. The human antibody or the antigen binding fragment thereof of claim 1, comprising:
a variable light chain amino acid sequence selected from the group consisting of:

(i)
```
                                       (SEQ ID NO: 28)
DIQMTQSPSS LSASVGDRVT ITCRASQGIR NHHAWYQQKP
GKAPKLLIYA ASTLQSGVPS RFSGSGSGTD FTLTISSLQP
EDVATYYCQR YNRAPYTFGQ GTKVEIK,
```

(ii)
```
                                       (SEQ ID NO: 29)
DIQMTQSPSS LSASVGDRVT ITCRASQGIR NYLAWYQQKP
GKAPKLLIYA ASTLQSGVPS RFSGSGSGTD FTLTISSLQP
EDVATYYCHH YHRAPYTFGQ GTKVEIK,
```

(iii)
```
                                       (SEQ ID NO: 30)
DIQMTQSPSS LSASVGDRVT ITCRASQGIR NYLAWYQQKP
GKAPKLLIYA ASTLQSGVPS RFSGSGSGTD FTLTISSLQP
EDVATYYCQH YHRAPYHFGQ GTKVEIK,
```

(iv)
```
                                       (SEQ ID NO: 33)
DIQMTQSPSS LSASVGDRVT ITCRASQGIR NYLAWYQQKP
GKAPKLLIYA ASTLQSGVPS RFSGSGSGTD FTLTISSLQP
EDVATYYCQH YHRAPYTFGQ GTKVEIK,
```

(v)
```
                                       (SEQ ID NO: 34)
DIQMTQSPSS LSASVGDRVT ITCRASQGIR NHLAWYQQKP
GKAPKLLIYA ASTLQSGVPS RFSGSGSGTD FTLTISSLQP
EDVATYYCQR YNHAPYTFGQ GTKVEIK,
```

(vi)
```
                                       (SEQ ID NO: 35)
DIQMTQSPSS LSASVGDRVT ITCRASQGIR NHLAWYQQKP
GKAPKLLIYA ASTLQSGVPS RFSGSGSGTD FTLTISSLQP
EDVATYYCQR YNRAPYTFGQ GTKVEIK,
```

(vii)
```
                                       (SEQ ID NO: 36)
DIQMTQSPSS LSASVGDRVT ITCRASQGIR NYLAWYQQKP
GKAPKLLIYA ASTLQSGVPS RFSGSGSGTD FTLTISSLQP
EDVATYYCQR HNRAPYTFGQ GTKVEIK,
and
```

(viii)
```
                                       (SEQ ID NO: 37)
DIQMTQSPSS LSASVGDRVT ITCRASQGIR NHLAWYQQKP
GKAPKLLIYA AHTLQSGVPS RFSGSGSGTD FTLTISSLQP
EDVATYYCQR YNRAPYTFGQ GTKVEIK,
and
``` a variable heavy chain amino acid sequence selected from the group consisting of:

(i)
```
                                       (SEQ ID NO: 25)
EVQLVESGGG LVQPGRSLRL SCAASGFTFD DYAMHWVRQA
PGKGLEWVSA ITWNSGHIDY ADSVEGRFTI SRDNAKNSLY
LQMNSLRAED TAVYYCAKVS YHSTASSLDY WGQGTLVTVS S;
```

(ii)
```
                                       (SEQ ID NO: 26)
EVQLVESGGG LVQPGRSLRL SCAASGFTFD DYAMHWVRQA
PGKGLEWVSA ITWNSGHIDY ADSVEGRFTI SRDNAKNSLY
LQMNSLRAED TAVYYCAKVS YLSTAHHLDY WGOGTLVTVS S;
and
```

(iii)
```
                                       (SEQ ID NO: 39)
EVQLVESGGG LVQPGRSLRL SCAASGFTFD DYAMHWVRQA
PGKGLEWVSA ITWNSGHIDY ADSVEGRFTI SRDNAKNSLY
LQMNSLRAED TAVYYCAKVH YHSTASSLDY WGQGTLVTVS S.
```

14. A human antibody or an antigen binding fragment thereof with a pH dependent antigen binding, comprising: light and heavy chain variable regions of a variant of human antibody adalimumab with the same or similar TNF-binding activity as human antibody adalimumab, wherein at least one of the CDR domains of the light chain variable region is mutated by replacing from one to four amino acids within said CDR domains by a histidine residue and/or the CDR-H3 domain of the heavy chain variable region is mutated by replacing one or more two amino acids within said CDR domains by a histidine residue, thereby generating a mutated adalimumab eliciting a significant pH dependent antigen binding, said mutated adalimumab comprising:
the variable heavy chain amino acid sequence

```
                                       (SEQ ID NO: 25)
EVQLVESGGG LVQPGRSLRL SCAASGFTFD DYAMHWVRQA
PGKGLEWVSA ITWNSGHIDY ADSVEGRFTI SRDNAKNSLY
LQMNSLRAED TAVYYCAKVS YHSTASSLDY WGQGTLVTVSS
and
``` the variable light chain amino acid sequence

```
                                       (SEQ ID NO: 27)
DIQMTQSPSS LSASVGDRVT ITCRASQGIR NHHAWYQQKP
GKAPKLLIYA ASTLQSGVPS RFSGSGSGTD FTLTISSLQP
EDVATYYCQR YNRAPYTFGQ GTKVEIK .
```

15. A human antibody or an antigen binding fragment thereof with a pH dependent antigen binding, comprising: light and heavy chain variable regions of a variant of human antibody adalimumab with the same or similar TNF-binding activity as human antibody adalimumab, wherein at least one of the CDR domains of the light chain variable region is mutated by replacing from one to four amino acids within said CDR domains by a histidine residue and/or the CDR-H3 domain of the heavy chain variable region is mutated by replacing one or two amino acids within said CDR domains by a histidine residue, thereby generating a mutated adalimumab eliciting a pH dependent antigen binding, said mutated adalimumab comprising:
the variable heavy chain amino acid sequence

```
                                       (SEQ ID NO: 26)
EVQLVESGGG LVQPGRSLRL SCAASGFTFD DYAMHWVRQA
PGKGLEWVSA ITWNSGHIDY ADSVEGRFTI SRDNAKNSLY
LQMNSLRAED TAVYYCAKVS YLSTAHHLDY WGQGTLVTVS S
and
``` the variable light chain amino acid sequence

```
                                       (SEQ ID NO: 28)
DIQMTQSPSS LSASVGDRVT ITCRASQGIR NYLAWYQQKP
GKAPKLLIYA ASTLQSGVPS RFSGSGSGTD FTLTISSLQP
EDVATYYCHH YHRAPYTFGQ GTKVEIK,
or
``` the variable light chain amino acid sequence

```
                                       (SEQ ID NO: 29)
DIQMTQSPSS LSASVGDRVT ITCRASQGIR NYLAWYQQKP
GKAPKLLIYA ASTLQSGVPS RFSGSGSGTD FTLTISSLQP
EDVATYYCQH YHRAPYHFGQ GTKVEIK.
```

16. The human antibody or the antigen binding fragment thereof of claim 1, comprising the human heavy chain IgG1 constant region of SEQ ID NO: 11.

17. The human antibody or the antigen binding fragment thereof of claim 16, wherein a Fc portion of said IgG1 constant region is mutated at one or more amino acid positions resulting in a respective antibody with modified FcRn binding.

18. The human antibody or the antigen binding fragment thereof of claim 16, comprising a human kappa constant region.

19. An antibody-drug conjugate comprising the human antibody or an antibody fragment thereof of claim 1 linked directly or indirectly to a cytotoxic chemical drug or recombinantly fused to a cytokine.

20. A pharmaceutical composition suitable for treatment of an inflammatory, autoimmune or cancer disease, comprising: the human antibody or the antigen binding fragment thereof of claim 1, or an antibody-drug conjugate comprising the antibody or the antibody fragment thereof of claim 1 linked directly or indirectly to a cytotoxic chemical drug or recombinantly fused to a cytokine together with a pharmaceutically acceptable carrier, diluent or excipient.

21. A method of treating a TNFα induced inflammatory, autoimmune or cancer disease, the method comprising:
administering an effective amount of the human antibody, or the antigen binding fragment thereof of claim 1 or an antibody-drug conjugate comprising the antibody or an antibody fragment thereof of claim 1 linked directly or indirectly to a cytotoxic chemical drug or recombinantly fused to a cytokine, to a subject in need thereof.

22. A method for manufacture of a medicament for treating a TNFα induced inflammatory, autoimmune or cancer disease, the method comprising:
mutating at least one of the CDR domains of the light chain variable region of human antibody adalimumab or a variant thereof having the same or similar TNF-binding activity by replacement of from one to four amino acids within the at least one of the CDR domains by a histidine residue and/or mutating the CDR-H3 domain of the heavy chain variable regions of human antibody adalimumab or a variant thereof having the same or similar TNF-binding activity by replacement of one or two amino acids within the CDR-H3 domain by a histidine residue, thereby generating a mutated adalimumab or adalimumab variant eliciting a pH dependent antigen binding with an antigen dissociation rate ($K_{dis}$) ratio pH 6/pH 7 measured by biolayer interferometry which is at least 5 fold higher compared to a respective $K_{dis}$ rate ratio of non-mutated adalimumab.

* * * * *

UNITED STATES PATENT AND TRADEMARK OFFICE
CERTIFICATE OF CORRECTION

PATENT NO. : 10,183,994 B2
APPLICATION NO. : 15/322893
DATED : January 22, 2019
INVENTOR(S) : Ralf Guenther et al.

Page 1 of 1

It is certified that error appears in the above-identified patent and that said Letters Patent is hereby corrected as shown below:

On the Title Page

Item (54) and in the Specification, at Column 1, Lines 1-3, Title is currently:
"ANTI-TNFα ANTIBODIES WITH PH-DEPENDENT ANTIGEN BINDING FOR IMPROVED TARGET CLEARENCE"

And should be:
--ANTI-TNFα ANTIBODIES WITH PH-DEPENDENT ANTIGEN BINDING FOR IMPROVED TARGET CLEARANCE--

Signed and Sealed this
Sixteenth Day of April, 2019

Andrei Iancu
*Director of the United States Patent and Trademark Office*